US010501769B2

(12) United States Patent
Franze et al.

(10) Patent No.: US 10,501,769 B2
(45) Date of Patent: Dec. 10, 2019

(54) METHOD FOR THE PRODUCTION OF A GLYCOSYLATED IMMUNOGLOBULIN

(71) Applicants: Hoffmann-La Roche Inc., Little Falls, NJ (US); Chugai Seiyaku Kabushiki Kaisha, Tokyo (JP)

(72) Inventors: Reinhard Franze, Penzberg (DE); Chikashi Hirashima, Tokyo (JP); Thomas Link, Penzberg (DE); Yoshinori Takagi, Tokyo (JP); Shinya Takuma, Tokyo (JP); Yuriko Tsuda, Tokyo (JP)

(73) Assignees: Hoffmann-La Roche Inc., Little Falls, NJ (US); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/844,570

(22) Filed: Sep. 3, 2015

(65) Prior Publication Data

US 2016/0186228 A1  Jun. 30, 2016

Related U.S. Application Data

(63) Continuation of application No. 12/911,300, filed on Oct. 25, 2010, now abandoned.

(30) Foreign Application Priority Data

Oct. 26, 2009 (EP) .................................. 09013455

(51) Int. Cl.
C12N 5/02 (2006.01)
C12P 21/00 (2006.01)
C07K 16/28 (2006.01)

(52) U.S. Cl.
CPC ........ *C12P 21/005* (2013.01); *C07K 16/2866* (2013.01); *C07K 2317/14* (2013.01); *C07K 2317/24* (2013.01); *C07K 2317/41* (2013.01); *C07K 2317/76* (2013.01)

(58) Field of Classification Search
CPC .................................................. C12P 21/005
See application file for complete search history.

(56) References Cited

U.S. PATENT DOCUMENTS

| | | |
|---|---|---|
| 3,926,723 A | 12/1975 | Green et al. |
| 4,657,863 A | 4/1987 | Maxwell et al. |
| 5,122,469 A | 6/1992 | Mather et al. |
| 5,171,840 A | 12/1992 | Kishimoto |
| 5,252,216 A | 10/1993 | Folena-Wasserman et al. |
| 5,316,938 A | 5/1994 | Keen et al. |
| 5,443,968 A | 8/1995 | Takazawa et al. |
| 5,480,796 A | 10/1996 | Kishimoto |
| 5,670,373 A | 9/1997 | Kishimoto et al. |
| 5,674,984 A | 10/1997 | Berman et al. |
| 5,795,965 A | 8/1998 | Tsuchiya et al. |
| 5,817,790 A | 10/1998 | Tsuchiya et al. |
| 5,821,121 A | 10/1998 | Brothers |
| 5,824,552 A | 10/1998 | Takazawa et al. |
| 5,851,793 A | 12/1998 | Kishimoto |
| 5,856,179 A | 1/1999 | Chen et al. |
| 5,888,510 A | 3/1999 | Kishimoto et al. |
| 5,981,260 A | 11/1999 | Metz |
| 5,990,282 A | 11/1999 | Kishimoto |
| 6,156,570 A | 5/2000 | Hu et al. |
| 6,086,874 A | 7/2000 | Yoshida et al. |
| 6,180,401 B1 | 1/2001 | Chen et al. |
| 6,238,891 B1 | 5/2001 | Maiorella et al. |
| 6,261,560 B1 | 7/2001 | Tsujinaka et al. |
| 6,284,453 B1 | 9/2001 | Siano |
| 6,338,964 B1 | 1/2002 | Matanguihan et al. |
| 6,372,493 B1 | 4/2002 | Brothers |
| 6,406,909 B1 | 6/2002 | Shibuya et al. |
| 6,410,691 B1 | 6/2002 | Kishimoto |
| 6,428,979 B1 | 8/2002 | Kishimoto |
| 6,492,163 B1 | 12/2002 | Yoo et al. |
| 6,537,782 B1 | 3/2003 | Shibuya et al. |
| 6,692,742 B1 | 2/2004 | Nakamura et al. |
| 6,723,319 B1 | 4/2004 | Ito et al. |
| 6,875,432 B2 | 4/2005 | Liu et al. |
| 6,962,812 B2 | 11/2005 | Shibuya et al. |
| 7,320,792 B2 | 1/2008 | Ito et al. |
| 7,332,289 B2 | 2/2008 | Takeda et al. |

(Continued)

FOREIGN PATENT DOCUMENTS

| | | |
|---|---|---|
| CA | 2417689 A1 | 9/2003 |
| CN | 1470632 A | 1/2004 |

(Continued)

OTHER PUBLICATIONS

Sauer et al. Biotechnol Bioeng 2000;67:585-97.*
Xie et al. Biotechnol Bioeng 1996;51:725-9.*
Pan et al. Cytotechnol 2017;69:39-56.*
U.S. Appl. No. 60/470,937, filed Jun. 15, 2003, Yen-Tung Luan, et al.
"European Search Report in EP09013455".
"International Search Report in PCT/EP2010/066073".
Altamirano et al., "Decoupling Cell Growth and Product Formation in Chinese Hamster Ovary Cells Through Metabolic Control" Biotechnology and Bioengineering 76:351-360 (2001).
Alton et al., "Direct utilization of mannose for mammalian glycoprotein biosynthesis" Glycobiology 8(3):285-295 ( 1998).

(Continued)

*Primary Examiner* — Scott Long
(74) *Attorney, Agent, or Firm* — Foley & Lardner LLP

(57) ABSTRACT

Herein is reported a method for the production of an immunoglobulin comprising the following steps: a) providing a eukaryotic cell comprising a nucleic acid encoding the immunoglobulin, b) cultivating the eukaryotic cell in a cultivation medium wherein the amount of glucose available in the cultivation medium per time unit is kept constant and limited to less than 80% of the amount that could maximally be utilized by the cells in the cultivation medium per time unit, and c) recovering the immunoglobulin from the culture.

41 Claims, 5 Drawing Sheets

(56) References Cited

U.S. PATENT DOCUMENTS

| | | | |
|---|---|---|---|
| 7,429,491 B2* | 9/2008 | Luan | C12N 5/0018 435/404 |
| 7,479,543 B2 | 1/2009 | Tsuchiya et al. | |
| 7,498,031 B2 | 3/2009 | Fujioka et al. | |
| 7,521,052 B2 | 4/2009 | Okuda et al. | |
| 7,566,453 B2 | 7/2009 | Nakamura et al. | |
| 7,666,413 B2 | 2/2010 | Liu et al. | |
| 7,771,723 B2 | 8/2010 | Nakamura et al. | |
| 7,824,674 B2 | 11/2010 | Ito et al. | |
| 7,927,815 B2 | 4/2011 | Takeda et al. | |
| 7,955,598 B2 | 6/2011 | Yoshizaki et al. | |
| 8,017,121 B2 | 9/2011 | Kishimoto et al. | |
| 8,142,776 B2 | 3/2012 | Liu et al. | |
| 8,173,126 B2 | 5/2012 | Yoshizaki et al. | |
| 8,227,195 B2 | 7/2012 | Stubenrauch et al. | |
| 8,398,980 B2 | 3/2013 | Kano et al. | |
| 8,420,789 B2 | 4/2013 | Takeda et al. | |
| 8,440,196 B1 | 5/2013 | Funakoshi et al. | |
| 8,470,316 B2 | 6/2013 | Yasunami | |
| 2001/0001663 A1 | 5/2001 | Kishimoto et al. | |
| 2001/0009767 A1 | 7/2001 | Ohman et al. | |
| 2002/0045571 A1 | 4/2002 | Liu et al. | |
| 2002/0119530 A1 | 8/2002 | Maiorella et al. | |
| 2002/0131967 A1 | 9/2002 | Nakamura et al. | |
| 2002/0187150 A1 | 12/2002 | Mihara et al. | |
| 2003/0170813 A1 | 9/2003 | Suga et al. | |
| 2003/0190316 A1 | 10/2003 | Kakuta et al. | |
| 2004/0048368 A1 | 3/2004 | Chen et al. | |
| 2004/0071706 A1 | 4/2004 | Ito et al. | |
| 2004/0115197 A1 | 6/2004 | Yoshizaki et al. | |
| 2004/0247621 A1 | 12/2004 | Nakamura et al. | |
| 2005/0070004 A1 | 3/2005 | Ishizaki et al. | |
| 2005/0070013 A1 | 3/2005 | Luan et al. | |
| 2005/0118163 A1 | 6/2005 | Mizushima et al. | |
| 2005/0142635 A1 | 6/2005 | Tsuchiya et al. | |
| 2005/0175603 A1 | 8/2005 | Liu et al. | |
| 2005/0214278 A1 | 9/2005 | Kakuta et al. | |
| 2005/0238644 A1 | 10/2005 | Mihara et al. | |
| 2006/0127975 A1* | 6/2006 | Link | C07K 14/70596 435/69.1 |
| 2006/0134113 A1 | 6/2006 | Mihara | |
| 2006/0142549 A1 | 6/2006 | Takeda et al. | |
| 2006/0165696 A1 | 7/2006 | Okano et al. | |
| 2006/0292147 A1 | 12/2006 | Yoshizaki et al. | |
| 2007/0036785 A1 | 2/2007 | Kishimoto et al. | |
| 2007/0098714 A1 | 5/2007 | Nishimoto et al. | |
| 2007/0116700 A1 | 5/2007 | Liu et al. | |
| 2007/0134242 A1 | 6/2007 | Nishimoto et al. | |
| 2007/0141675 A1 | 6/2007 | Suga et al. | |
| 2007/0148169 A1 | 6/2007 | Yoshizaki et al. | |
| 2007/0243189 A1 | 10/2007 | Yoshizaki et al. | |
| 2007/0280945 A1 | 12/2007 | Stevens et al. | |
| 2008/0124325 A1 | 5/2008 | Ito et al. | |
| 2008/0124761 A1 | 5/2008 | Goto et al. | |
| 2008/0274106 A1 | 6/2008 | Nishimoto et al. | |
| 2008/0255342 A1 | 10/2008 | Takeda et al. | |
| 2008/0306247 A1 | 12/2008 | Mizushima et al. | |
| 2009/0022716 A1 | 1/2009 | Rockwell et al. | |
| 2009/0022719 A1 | 1/2009 | Mihara et al. | |
| 2009/0028784 A1 | 1/2009 | Garcia-Martinez et al. | |
| 2009/0061466 A1 | 3/2009 | Hoesel et al. | |
| 2009/0131639 A1 | 5/2009 | Kakuta et al. | |
| 2009/0181029 A1 | 7/2009 | Okuda et al. | |
| 2009/0220499 A1 | 9/2009 | Yasunami | |
| 2009/0220500 A1 | 9/2009 | Kobara | |
| 2009/0263384 A1 | 10/2009 | Okada et al. | |
| 2009/0269335 A1 | 10/2009 | Nakashima et al. | |
| 2009/0291076 A1 | 11/2009 | Morichika et al. | |
| 2009/0311718 A1 | 12/2009 | Fukushima et al. | |
| 2010/0008907 A1 | 1/2010 | Nishimoto et al. | |
| 2010/0034811 A1 | 2/2010 | Ishida | |
| 2010/0061986 A1 | 3/2010 | Takahashi et al. | |
| 2010/0129355 A1 | 5/2010 | Ohguro et al. | |
| 2010/0129357 A1 | 5/2010 | Garcia-Martinez et al. | |
| 2010/0247523 A1 | 9/2010 | Kano et al. | |
| 2010/0255007 A1 | 10/2010 | Mihara et al. | |
| 2010/0285011 A1 | 11/2010 | Morichika et al. | |
| 2010/0291627 A1 | 11/2010 | Yamada et al. | |
| 2010/0304400 A1 | 12/2010 | Stubenrauch et al. | |
| 2011/0053223 A1 | 3/2011 | Bayer et al. | |
| 2011/0117087 A1 | 5/2011 | Franze et al. | |
| 2011/0150869 A1 | 6/2011 | Mitsunaga et al. | |
| 2011/0206664 A1 | 8/2011 | Yoshizaki et al. | |
| 2011/0245473 A1 | 10/2011 | Igawa et al. | |
| 2011/0262462 A1 | 10/2011 | Platt et al. | |
| 2011/0268734 A1 | 11/2011 | Ito et al. | |
| 2012/0009177 A1 | 1/2012 | Platt et al. | |
| 2012/0064086 A1 | 3/2012 | Liu et al. | |
| 2012/0076783 A1 | 3/2012 | Liu et al. | |
| 2012/0183539 A1 | 7/2012 | Maeda | |
| 2012/0219974 A1 | 8/2012 | Stubenrauch et al. | |
| 2012/0301460 A1 | 11/2012 | Bao et al. | |
| 2014/0329277 A1* | 11/2014 | Link | C12N 5/0018 435/69.6 |

FOREIGN PATENT DOCUMENTS

| | | |
|---|---|---|
| EP | 409607 | 1/1991 |
| EP | 05 677 38 A2 | 11/1993 |
| EP | 0567738 A2 | 11/1993 |
| EP | 0 387 840 B1 | 7/1994 |
| EP | 0387840 B1 | 7/1994 |
| EP | 628639 | 12/1994 |
| EP | 1 585 810 B1 | 3/2010 |
| EP | 1585810 B1 | 3/2010 |
| FI | 922172 A | 5/1992 |
| FI | 931969 A | 11/1993 |
| JP | 1101882 A | 4/1989 |
| JP | 06-292592 A | 10/1994 |
| JP | 7258252 | 10/1995 |
| JP | 08099902 | 4/1996 |
| JP | H05/227970 | 9/1996 |
| JP | 2001101882 A | 4/2001 |
| JP | 2002-335946 A | 11/2002 |
| JP | 2003-274934 A | 9/2003 |
| JP | 03630453 B2 | 3/2005 |
| JP | 03822137 B2 | 9/2006 |
| JP | 2009092508 A | 4/2009 |
| WO | WO 89/004867 A1 | 6/1989 |
| WO | 92/19759 | 11/1992 |
| WO | 93/22448 | 11/1993 |
| WO | WO 1993/122448 | 11/1993 |
| WO | WO 94/26087 A2 | 11/1994 |
| WO | WO 95/12664 A1 | 5/1995 |
| WO | WO 95/22599 A1 | 8/1995 |
| WO | 96/39488 | 12/1996 |
| WO | 97/26334 | 7/1997 |
| WO | 98/41611 | 9/1998 |
| WO | 2000/10607 A1 | 3/2000 |
| WO | WO 01/77140 A2 | 10/2001 |
| WO | WO 01/92555 A1 | 12/2001 |
| WO | 02/02793 | 1/2002 |
| WO | WO 2002/002793 | 1/2002 |
| WO | 2002/013859 A1 | 2/2002 |
| WO | WO 02/40697 A2 | 5/2002 |
| WO | WO 02/42471 A2 | 5/2002 |
| WO | WO 02/61108 A2 | 8/2002 |
| WO | 02/076578 | 10/2002 |
| WO | 02/101019 | 12/2002 |
| WO | WO 03/009858 A1 | 2/2003 |
| WO | WO 03/066816 A2 | 8/2003 |
| WO | WO 2002/033109 | 9/2003 |
| WO | WO 03/101224 A1 | 12/2003 |
| WO | WO 2004/005525 A2 | 1/2004 |
| WO | WO 2004/005527 A1 | 1/2004 |
| WO | WO 2004/041216 | 5/2004 |
| WO | 2004/048556 | 6/2004 |
| WO | 2004/104186 A1 | 12/2004 |
| WO | WO 2004/104186 | 12/2004 |
| WO | WO 2005/024000 A1 | 3/2005 |
| WO | 2005/061000 | 7/2005 |
| WO | WO-2007/087384 A2 | 8/2007 |
| WO | 2009-53366 | 10/2007 |
| WO | 2008/016134 A1 | 2/2008 |

(56) References Cited

FOREIGN PATENT DOCUMENTS

| WO | 2008078715 A1 | 7/2008 |
|---|---|---|
| WO | 2009/014263 | 1/2009 |
| WO | 2009/044774 | 4/2009 |
| WO | 2009/077127 | 6/2009 |
| WO | 2009/084659 | 9/2009 |
| WO | 2009/112250 | 9/2009 |
| WO | WO 2009/114641 | 9/2009 |
| WO | WO 2009114641 A1 | 9/2009 |
| WO | 2011/149046 A1 | 1/2011 |
| WO | 2011/149051 A1 | 1/2011 |
| WO | WO 2011/051231 | 5/2011 |
| WO | WO 2012/064627 A2 | 5/2012 |
| WO | 2013/031237 A1 | 3/2013 |

OTHER PUBLICATIONS

Ashwell and Harford, "Carbohydrate-specific receptors of the liver" Annu Rev Biochem 51:531-554 ( 1982).
Baenziger, J., "The role of glycosylation in protein recognition" Am J Pathol 121:382-391 ( 1985).
Baker et al., "Metabolic Control of Recombinant Protein N-Glycan Processing in NS0 and CHO Cells" Biotechnology and Bioengineering 73:188-202 (2001).
Baumann et al., "Glucose Starvation Leads in Rat Hepatoma Cells to Partially N-Glycosylated Glycoproteins Including α₁-Acid Glycoproteins" The Journal of Biological Chemistry 258:3942-3949 (1983).
Bernard, A.R. Production of Proteins by Transient Expression, Serono Pharmaceutical Research Institute, Chapter 17, pp. 605-626.
Borys et al., "Culture pH Affects Expression Rates and Glycosylation of Recombinant Mouse Placental Lactogen Proteins by Chinese Hamster Ovary (CHO) Cells" Bio/Technology 11:720-724 (Jun. 1993).
Bradshaw et al., "The hormonal control of protein N-glycosylation in the developing rabbit mammary gland and its effect upon transferrin synthesis and secretion" Biochim Biophys Acta 847:344-351 ( 1985).
Butler, M., "Animal cell cultures: recent achievements and perspectives in the production of biopharmaceuticals" Appl Microbiol Biotechnol. 68:283-291 ( 2005).
Chan and Wolf, "The role of vitamin A in the glycosylation reactions of glycoprotein synthesis in an 'in vitro' system" Biochem J 247:53-62 ( 1987).
Chapman et al., "Effects of glucose starvation and puromycin treatment on lipid-linked oligosaccharide precursors and biosynthetic enzymes in Chinese hamster ovary cells in vivo and in vitro" Archives of Biochemistry and Biophysics 260(1):320-333 (Jan. 1988).
Crowley, J., "Effect of dilution rate on the metabolism and product formation" Animal Cell Culture and Production of Biologicals, Kensington, AU:University of NSW pp. 275-281 (1991) .
Cruz et al., "Metabolic Shifts by Nutrient Manipulation in Continuous Cultures of BHK Cells." Biotechnol. Bioeng. 66:104-113 (1999).
Cruz et al., "Metabolic Shifts Do Not Influence the Glycosylation Patterns of a Recombinant Fusion Protein Expressed in BHK Cells" Biotechnology and Bioengineering 69:129-139 (2000).
Dalili et al., "Glutamine-Limited Batch Hybridoma Growth and Antibody Production: Experiment and Model" Biotechnology and Bioengineering 36(36):74-82 (1990).
Davidson et al., "Sindbis Virus Glycoproteins are Abnormally Glycosylated in Chinese Hamster Ovary Cells Deprived of Glucose" J. Gen. Virol. 66:1457-1468 (1985) .
De Buyl et al., "Fed-Batch Culture Development" New Developments and New Applications in Animal Cell Technology, Netherlands:Kluwer Academic Publishers pp. 337-342 (1998).
De Tremblay et al., "Optimization of fed-batch culture of hybridoma cells using dynamic programming: Single and multi feed cases" Bioprocess Engineering 7:229-234 (1992).

Dowd et al., "Glucose-Based Optimization of CHO-Cell Perfusion Cultures" Biotechnology and Bioengineering 75:252-256 (2001).
Dowd et al., "Predictive Control of Hollow-Fiber Bioreactors for the Production of Monoclonal Antibodies" Biotechnology and Bioengineering 63:484-492 (1999).
Dwek et al., "Glycobiology: 'the function of sugar in the IgG molecule'" J Anat 187:279-292 (Oct. 1995).
Elbein, A., "Inhibitors of the Biosynthesis and Processing of N-Linked Oligosaccharides" CRC Critical Reviews 16(1):21-49 (1984).
Elbein, A., "Inhibitors of the Biosynthesis and Processing of N-Linked Oligosaccharide Chains" Annual Review of Biochemistry 56:497-534 (1987).
Endo et al., "Glycosylation of the variable region of immunoglobulin G-site specific maturation of the sugar chains" Mol Immunol 32(13):931-940 ( 1995).
Essers et al., "Bioprocess development for the production of a prospective tumor vaccine expressed by CHO cells in protein-free medium" Poster LifeTec Xchange Congress 'Technologies for Life Sciences', Aachen, Germany, pp. 1 (2003).
Feizi and Childs, "Carbohydrates as antigenic determinants of glycoproteins" Biochem J 245:1-11 ( 1987).
Fleischaker, R.J., "An Experimental Study in the Use of Instrumentation to Analyze Metabolism and Product Formation in Cell Culture" Ph.D. Thesis Submitted to Massachusetts Institute of Technology (Jun. 1982).
Frahm et al., "Adaptive, Model-Based Control by the Open-Loop-Fedback-Optimal (OLFO) Controller for the Effective Fed-Batch Cultivation of Hybridoma Cells" Biotechnology Progress 18:1095-1103 (2002).
Frame et al., "Oxygen Uptake of Mammalian Cells in Microcarrier Culture—Response to Changes in Glucose Concentration" Biotechnology Letters 7(3):147-152 (1985).
Gambhir et al., "Alteration of Cellular Metabolism by Consecutive Fed-Batch Cultures of Mammalian Cells" Journal of Bioscience and Bioengineering 87(6):805-810 (1999).
Gawlitzek et al., "Characterization of changes in the glycosylation pattern of recombinant proteins from BHK-21 cells due to different culture conditions" Journal of Biotechnology 42:117-131 (1995).
Gawlitzek et al., "Effect of Different Cell Culture Conditions on the Polypeptide Integrity and N-Glycosylation of a Recombinant Model Glycoprotein" Biotechnology and Bioengineering 46:536-544 (1995).
Genentech, Inc., "ACTEMRA (tocilizumab) Injection, for intravenous infusion" (U.S. Prescribing Information) pp. 1-24 (2010).
Genovese et al., "Interleukin-6 receptor inhibition with tocilizumab reduces disease activity in rheumatoid arthritis with inadequate response to disease-modifying antirheumatic drugs: The tocilizumab in combination with traditional disease-modifying antirheumatic drug therapy study" Arthritis & Rheumatism 58(10):2968-2980 (Oct. 2008).
Gershman et al., "Transitory Effects of Glucose Starvation on the Synthesis of Dolichol-linked Oligosaccharides in Mammalian Cells" The Journal of Biological Chemistry 256(15):7774-7780 (1981).
Glacken, M.W., "Development of Mathematical Descriptions of Mammalian Cell Culture Kinetics for the Optimization of Fed-Batch Bioreactors" Ph.D. Thesis submitted to Massachusetts Institute of Technology for the Degree of Doctor of Science in Biochemical Engineering (Apr. 1987).
Goetze et al., "High-mannose glycans on the Fc region of therapeutic IgG antibodies increase serum clearance in humans" Glycobiology 21(7):949-959 (Jul. 2011).
Griffiths, B., "Perfusion Systems for Cell Cultivation" Large-Scale Mammalian Cell Culture Technology, Lubiniecki, A.S., New York and Basel:Marcel Dekker, Inc., Chapter 9, pp. 217-250 (1990).
Guan et al., "On-line heatflux measurements improve the culture medium for the growth and productivity of genetically engineered CHO cells" Cytotechnology 30:107-120 (1999).
Guardia et al., "Cybernetic Modeling and Regulation of Metabolic Pathways in Multiple Steady States of Hybridoma Cells" Biotechnology Progress 16:847-853 (2000).
Hahn et al., "Growth-associated Glycosylation of Transferrin Secreted by HepG2 Cells" The Journal of Biological Chemistry 267:23982-23987 (1992).

(56) References Cited

OTHER PUBLICATIONS

Hayter et al., "Chinese Hamster Ovary Cell Growth and Interferon Production Kinetics in Stirred Batch Culture" Applied Microbiology and Biotechnology 34:559-564 (1991).
Hayter et al., "Glucose-Limited Chemostat Culture of Chinese Hamster Ovary Cells Producing Recombinant Human Interferon-γ" Biotechnology and Bioengineering 39:327-335 (1992).
Higareda et al., "The Use of Culture Redox Potential and Oxygen Uptake Rate for Assessing Glucose and Glutamine Depletion in Hybridoma Cultures" Biotechnology and Bioengineering 56:555-563 (1997).
Hills et al., "Metabolic control of recombinant monoclonal antibody N-glycosylation in GS-NS0 cells" Biotechnol Bioeng 75:239-251 ( 2001).
Hu et al., "Effect of Glucose on the Cultivation of Mammalian Cells" 7th General Meeting of ESACT on Advances in Animal Cell Technology: Cell Engineering, Evaluation and Exploitation, Baden, Austria 66:279-290 (1987).
Ip et al., "Structural characterization of the N-glycans of a humanized anti-CD18 murine immunoglobulin G" Arch Biochem Biophys 308(2):387-399 (Feb. 1994).
Jefferis et al., "Glycosylation of antibody molecules: structural and functional significance" Chem. Immunol. 65:111-128 (1997).
Jefferis, Royston, "Glycosylation of recombinant antibody therapeutics" Biotechnol Prog 21(1):11-16 (Jan. 2005).
Jenkins et al., "Getting the glycosylation right: Implications for the biotechnology industry" Nature Biotechnology 14:975-981 (1996).
Kanda et al., "Comparison of biological activity among nonfucosylated therapeutic IgG1 antibodies with three different N-linked Fc oligosaccharides: the high-mannose, hybrid, and complex types" Glycobiology 17(1):104-118 ( 2006).
Kitos et al., "Glucose Metabolism by Mouse Cells (NCTC Clone 929) Under Conditions of Defined Nutrition" Experimental Cell Research 35:108-118 (1964).
Kleman et al., "A Predictive and Feedback Control Algorithm Maintains a Constant Glucose Concentration in Fed-Batch Fermentations" Applied and Environmental Microbiology 57(4):910-917 (1991).
Kompala et al., "Optimization of High Cell Density Perfusion Bioreactors" Cell Culture Technology for Pharmaceutical and Cell-Based Therapies, Ozturk, S.S. and Hu, W.S. (eds.), Chapter 11, pp. 387-416 (2006).
Kondo et al., "Improved Method for Fluorescence Labeling of Sugar Chains with Sialic Acid Residues" Agricultural and Biological Chemistry 54:2169-2170 (1990).
Konstantinov et al., "Advantages and Disadvantages of Glucose Limitation in Perfused Mammalian Cell Cultures: Analysis of a Large-Scale, High-Density Myeloma Cultivation" Animal Cell Technology—Developments to the 21st Century, Beuvery et al. (eds.), Kluwer Academic Publishers pp. 567-573 (1995).
Krapp et al., "Structural analysis of human IgG-Fc glycoforms reveals a correlation between glycosylation and structural integrity" J Mol Biol 325(5):979-989 (Jan. 31, 2003).
Kunkel et al., "Dissolved oxygen concentration in serum-free continuous culture affects N-linked glycosylation of a monoclonal antibody" J Biotechnol 62:55-71 ( 1998).
Kurokawa et al., "Growth Characteristics in Fed-Batch Culture of Hybridoma Cells with Control of Glucose and Glutamine Concentrations" Biotechnology and Bioengineering 44:95-103 (1994).
Kurokawa et al., "Kinetic Study of Hybridoma Metabolism and Antibody Production in Continuous Culture Using Serum-Free Medium" Journal of Fermentation and Bioengineering 76(2):128-133 (1993).
Lin et al., "Determination of the Maximum Specific Uptake Capacities for Glucose and Oxygen in Glucose-Limited Fed-Batch Cultivations of *Eschericia coli*" Biotechnology and Bioengineering 73:347-357 (2001).
Lin et al., "Production of tPA in Recombinant CHO Cells Under Oxygen-Limited Conditions" Biotechnology and Bioengineering 42:339-350 (1993).

Link et al., "Development of a Metabolically Optimized Fermentation Process Based on Glucose-Limited CHO Perfusion Culture" Animal Cell Technology meets Genomics pp. 423-430 (2005).
Link et al., "Process Development for the Large Scale Production of human Mucins with recombinant CHO Cells" Slides 7th Int. Workshop on Carcinoma-associate mucins, Crete, Greece, pp. 1-4 ( Apr. 3,2003).
Ljunggren et al., "Specific growth rate as a parameter for tracing growth-limiting substances in animal cell cultures" Journal of Biotechnology 42:163-175 (1995).
Lonza, ProCHO///superscript:TM/// Protein-free CHO Medium, pp. 1 (Retrieved on internet Nov. 30, 2009).
Lund et al., "Control of IgG/Fc Glycosylation: A Comparison of Oligosaccharides from Chimeric Human/Mouse and Mouse Subclass Immunoglobulin Gs" Mol Immunol 30(8):741-748 ( 1993).
Lund et al., "Multiple Interactions of the IgG with Its Core Oligosaccharide Can Modulate Recognition by Complement and Human Fcγ Receptor I and Influence the Synthesis of Its Oligosaccharide Chains" J Immunol 157:4963-4969 ( 1996).
Lund et al., "Oligosaccharide-protein interactions in IgG can modulate recognition by Fcγ receptors" FASEB J 9:115-119 ( 1995).
Lydersen, B.K., "Perfusion Cell Culture System Based on Ceramic Matrices" Large Scale Animal Culture, Munich:Hanser Publishers pp. 169-192 (1987).
Marique et al., "A general artificial neural network for the modelization of culture kinetics of different CHO strains" Cytotechnology 36:55-60 (2001).
Mather et al., "Culture Media, Animal Cells, Large Scale Production" Encyclopedia of Bioprocess Technology: Fermentation, Biocatalysis, and Bioseparation, Flickinger, M.C. and Drew, S.W., John Wiley & Sons, Inc. vol. 2:777-785 (1999).
McFarlane, I.G., "Hepatic clearance of serum glycoproteins" Clin Sci 64:127-135 ( 1983).
Meijer et al., "Effects of Glucose Supply on Myeloma Growth and Metabolism in Chemostat Culture" Journal of Cellular Physiology 162:191-198 (1995).
Millward et al., "Effect of constant and variable domain glycosylation on pharmacokinetics of therapeutic antibodies in mice" Biologicals 36:41-47 ( 2008).
Mimura et al. et al., "The influence of glycosylation on the thermal stability and effector function expression of human IgG1-Fc: properties of a series of truncated glycoforms" Mol Immunol 37(12-13):697-706 (Aug. 2000).
Mimura et al., "Role of Oligosaccharide Residues of IgG1-Fc in FcγRIIb Binding" J Biol Chem 276(49):45539-45547 (Dec. 7, 2001).
Mizuochi et al., "Structures of the sugar chains of mouse immunoglobulin G ¹" Arch Biochem Biophys 257(2):387-394 ( 1987).
Muthing et al., "Effects of Buffering Conditions and Culture pH on Production Rates and Glycosylation of Clinical Phase I Antimelanoma Mouse IgG3 Monoclonal Antibody R24" Biotechnology and Bioengineering 83:321-334 (2003).
Nielsen et al., "Avoiding rapid growth at high cell densities: A potentially important optimisation criterion for hybridoma cultures" Cytotechnology 9:21-27 (1992).
Noll, T., "Development of a Metabolically Optimized Fermentation Process Based on Glucose-limited CHO Perfusion Culture" Oral Presentation at ESACT Meeting (2003).
Noll, T., "Glucose limitation in mammalian cell culture: starvation to success?—Development of a metabolically optimized fermentation process based on CHO perfusion culture" Slides JAACT, Nagoya, Japan, pp. 1-32 ( Nov. 16, 2004).
Noll, T., "Glucose-limited mammalian cell culture for the production of recombinant proteins" Slides Workshop on 'Production of biopharmaceuticals in animal cell cultures', Rio de Janeiro, Brazil, pp. 1-50 ( Jul. 13, 2004).
Noll, T., "Produktion rekombinanter Proteine mit Säugerzellen—Beiträge zur Prozessentwicklung" Slides Probiogen AG, Berlin, Germany, pp. 1-31 ( Jun. 24, 2003).
Noll, T., "Produktion rekombinanter Proteine mit Säugerzellen—Beiträge zur Prozessentwicklung" Slides Penzberg, Germany, pp. 1-37 ( Jan. 31, 2003).

(56) References Cited

OTHER PUBLICATIONS

Noll, T., "Vervielfachung der Produktivität von Cho Zellen durch eine neue Prozessstrategie" Slides GVC/Dechema Vortrags—und Diskussionstagung 'Zellkulturen: Vom biologischen System zum Produktionsprozess', Bad Dürkheim, Germany, pp. 1-32 ( May 26, 2003).
Omasa et al., "Effects of Lactate Concentration on Hybridoma Culture in Lactate-Controlled Fed-Batch Operation" Biotechnology and Bioengineering 39:556-564 (1992).
Parekh et al., "Association of rheumatoid arthritis and primary osteoarthritis with changes in the glycosylation pattern of total serum IgG" Nature 316:452-457 ( 1985).
Patel et al., "Different culture methods lead to differences in glycosylation of a murine IgG monoclonal antibody" Biochemistry J 285:839-845 ( 1992).
Peipp et al., "Molecular Engineering III: Fc Engineering" Handbook of Therapeutic Antibodies, Stefan Dubel, Wiley-VCH pp. 171-196 (2007).
Rearick et al., "Glucose Starvation Alters Lipid-linked Oligosaccharide Biosynthesis in Chinese Hamster Ovary Cells" The Journal of Biological Chemistry 256:6255-6261 (1981).
Rifai et al., "The N-Glycans Determine the Differential Blood Clearance and Hepatic Uptake of Human Immunoglobulin (Ig)A1 and IgA2 Isotypes" J Exp Med 191:2171-2181 ( 2000).
Robinson et al., "Characterization of a Recombinant Antibody Produced in the Course of a High Yield Fed-Batch Process" Biotechnol Bioeng 44:727-735 ( 1994).
Roche, "RoActemra 20 mg/ml concentrate for solution for infusion" (EU Prescribing Information) pp. 1-14 (2009).
Saba et al., "A study of immunoglobulin G glycosylation in monoclonal and polyclonal species by electrospray and matrix-assisted laser desorption/ionization mass spectrometry" Anal Biochem 305:16-31 ( 2002).
Schauer, R., "Sialic acids as antigenic determinants of complex carbohydrates" Adv Exp Med Biol 228:47-72 ( 1988).
Schumpp et al., "Growth Study of Lactate and Ammonia Double-Resistant Clones of HL-60 Cells" Animal Cell Technology pp. 183-185 (1992).
Senger et al., "Optimization of fed-batch parameters and harvest time of CHO cell cultures for a glycosylated product with multiple mechanisms of inactivation." Biotechnol Bioeng. 98(2):378-390 (Oct. 1, 2007).
Stark et al., "Glucose-Dependent Glycosylation of Secretory Glycoprotein in Mouse Myeloma Cells" Archives of Biochemistry & Biophysics 192:599-609 (1979).
Strube et al., "Carbohydrate Structure of Glycoprotein 52 Encoded by the Polycythemia-inducing Strain of Friend Spleen Focus-forming Virus" The Journal of Biological Chemistry 263:3762-3771 (1988).
Sugiura et al., "Dynamics of recombinant protein production by mammalian cells in immobilized perfusion culture" Enzyme and Microbial Technology 22:699-704 ( 1998).
Tachibana et al., "Changes of monosaccharide availability of human hybridoma lead to alteration of biological properties of human monoclonal antibody" Cytotechnology 16:151-157 ( 1994).
Taga et al., "Analysis of an antibody pharmaceutical, tocilizumab, by capillary electrophoresis using a carboxylated capillary" J. Sep. Sci. 31:853-858 ( 2008).
Takuma et al., "Dependence on Glucose Limitation of the pCO$_2$ Influences on CHO Cell Growth, Metabolism and IgG Production" Biotechnology and Bioengineering 97(6):1479-1488 (Aug. 2007).
Taniguchi et al., "Structures of the sugar chains of rabbit immunoglobulin G: Occurrence of asparagine-linked sugar chains in Fab fragment" Biochem 24:5551-5557 ( 1985).
Turco, "Modification of oligosaccharide-lipid synthesis and protein glycosylation in glucose-deprived cells" Arch Biochem Biophys 205(2):330-339 (Dec. 1980).
Venkiteshwaran, A., "Tocilizumab" mAbs 1(5):432-438 (2009).
Vijayalakshmi, "Antibody purification methods" Appl Biochem Biotech 75:93-102 ( 1998).
Werner et al. et al., "Safety and economic aspects of continuous mammalian cell culture" J Biotechnol 22:51-68 ( 1992).
West, C.M., "Current ideas on the significance of protein glycosylation" Mol Cell Biochem 72:3-20 ( 1986).
Wong et al., "Impact of Dynamic Online Fed-Batch Strategies on Metabolism, Productivity and N-Glycosylation Quality in CHO Cell Cultures" Biotechnology and Bioengineering 89:164-177 (2005).
Wright and Morrison, "Effect of C2-associated carbohydrate structure on Ig effector function: Studies with chimeric mouse-human IgG1 antibodies in glycosylation mutants of Chinese Hamster Ovary cells" J Immunol 160:3393-3402 ( 1998).
Wright et al., "In vivo trafficking and catabolism of IgG1 antibodies with Fc associated carbohydrates of differing structure" Glycobiology 10(12):1347-1355 ( 2000).
Xie et al., "Fed-Batch Cultivation of Animal Cells Using Different Medium Design Concepts and Feeding Strategies" Biotechnology and Bioengineering 43:1175-1189 (1994).
Xie et al., "Fed-Batch Cultivation of Mammalian Cells for the Production of Recombinant Proteins" (Merck Research Laboratories), Chapter 10, pp. 349-386.
Xie et al., "Gamma-interferon production and quality in stoichiometric fed-batch cultures of Chinese Hamster Ovary (CHO) cells under serum-free conditions" Biotechnology and Bioengineering 56(5):577-582 (Dec. 5, 1997).
Xie et al., "Integrated approaches to the design of media and feeding strategies for fed-batch cultures of animal cells" Tibtech 15:109-113 (1997).
Yamane et al., "Fed-batch Techniques in Microbial Processes" Adv. Biochem. Eng. Biotechnol. 30:147-194 (1984).
Youings et al., "Site-specific glycosylation of human immunoglobulin G is altered in four rheumatoid arthritis patients" Biochem J 314:621-630 ( 1996).
Yu et al., "Production, characterization, and pharmacokinetic properties of antibodies with N-linked mannose-5 glycans" MAbs 4(4):475-487 (Jul. 2012).
Zeng et al., "Cell Culture Kinetics and Modeling" GBF National Research Institute for Biotechnology, Braunschweig, Chapter 9, pp. 299-348.
Zeng et al., "Variation of Stoichiometric Ratios and Their Correlation for Monitoring and Control of Animal Cell Cultures" Biotechnology Progress 14:434-441 (1998).
Zeng, "Mathematical Modeling and Analysis of Glucose and Glutamine Utilization and Regulation in Cultures of Continuous Mammalian Cells" Biotechnology and Bioengineering 47:334-346 (1995).
Zhou et al., "Alteration of Mammalian Cell Metabolism by Dynamic Nutrient Feeding" Cytotechnology 24:99-108 (1997).
Zhou et al., "High Viable Cell Concentration Fed-Batch Cultures of Hybridoma Cells Through On-Line Nutrient Feeding" Biotechnology and Bioengineering 46:579-587 (1995).
Zhou et al., "On-Line Characterization of Hybridoma Cell Culture Process" Biotechnology and Bioengineering 44:170-177 (1994).
Zielke et al., "Reciprocal Regulation of Glucose and Glutamine Utilization by Cultured Human Dipoid Fibroblasts" Journal of Cellular Physiology 95:41-48 (1978).
Zuckier et al., "Chimeric human-mouse IgG antibodies with shuffled constant region exons demonstrate that multiple domains contribute to in vivo half-life" Cancer Res 58:3905-3908 ( 1998).
Åkesson, et. al., "Probing control of fed-batch cultivations: analysis and tuning", Control Engineering Practice, 2001, vol. 9, pp. 709-723.
Barford, et. al., "Enhancement of Productivity by Yield Improvements Using Simulation Techniques", Animal Cell Technology: Basic and Applied Aspects, H. Murakami, et. al., Kluwer Academic Publishers, 1992, pp. 397-403.
Bilbia, et. al., "In Pursuit of the Optimal Fed-Batch Process for Monoclonal Antibody Production", Biotechnol. Prog., 1995, vol. 11, pp. 1-13.
Communication of the Examination Division of May 8, 2007 relating to ep 04 752 591.0 (5 pages).
De Buyl, et. al., "Fed-batch culture development based on biomass monitoring", New Developments and New Applications in Animal Cell Technology, O.W. Merlen, et. al., Kluwer Academic Publishers, 1998, pp. 337-342.

(56) References Cited

OTHER PUBLICATIONS

De Tremblay, et. al., "Fed-batch culture of hybridoma cells: comparison of optimal control approach and closed loop strategies", Bioprocess Engineering, 1993, vol. 9, pp. 13-21.
Declaration of Dr. Christoph Holzke dated Jul. 26, 2013 (1 page).
Exhibit A in Declaration of Dr. Christoph Holzke, internal database cataloguing and warehousing system confirming receipt of Thesis by Thomas Link dated Mar. 11, 2004 (1 page).
Declaration of Dr. Denis Drapeau dated Dec. 3, 2012 (7 pages).
Domach, et. al., Computer Model for Glucose-Limited Growth of a Single Cell of *Escherichia coli* Br/a, Biotechnol. and Bioeng., 1984, vol. XXVI, 203-216.
EP Search Report in EP 10176622 dated Apr. 19, 2012.
EP Search Report in EP10152393 dated Jul. 27, 2010.
Europa, et. al., "Multiple Steady States with Distinct Cellular Metabolism in Continuous Culture of Mammalian Cells", Biotechnology and Bioengineering, 2000, vol. 67, pp. 25-34.
Excerpt from Biochrom Product Information Catalogue, "Ham's F-12 liquid medium", 2015, p. 47.
Fu, et. al., "Metabolic Flux Distributions in Hybridoma Cells at Different Metabolic Rates", Animal Cell Technology Developments Towards the 21st Century, 1999, pp. 51-55.
Glacken, et. al., "Mathematical descriptions of hybridoma culture kinetics. III. Simulation of fed-batch bioreactors", Journal of Biotechnology, 1989, vol. 10, pp. 39-66.
Glacken, et. al., "Reduction of Waste Product Excretion via Nutrient Control: Possible Strategies for Maximizing Product and Cell Yields on Serum in Cultures of Mammalian Cells", Biotechnol. and Bioengineering, 1986, vol. XXVII, pp. 1376-1389.
Häggström, et. al., "Metabolic Engineering of Animal Cells", Annals of the New York Academy of Sciences, 1996, vol. 782, pp. 40-52.
Hayter, et. al., "Glucose-Limited Chemostat Culture of Chinese Hamster Ovary Cells Producing Recombinant Human Interferon-γ", Biotechnol. and Bioengineering, 1992, vol. 39, pp. 327-335.
Hu, et. al., "Controlling Mammalian Cell Metabolism in Bioreactors", J. Microbiol. Biotechnol., 1998, vol. 8, No. 1, pp. 8-13.
Hu, et. al., "Toward Advanced Nutrient Feeding in Animal Cell Culture", Harnessing Biotechnology for the 21st Century, 1992, pp. 202-205.
Kleman, et. al., "A Predictive and Feedback Control Algorithm Maintains a Constant Glucose Concentration in Fed-Batch Fermentations", Applied and Environmental Microbiology, Apr. 1991, vol. 57, No. 4, pp. 910-917.
Lee, et. al., "Control of fed batch fermentations", Biotechnology Advances, 1999, vol. 17, pp. 29-48.
Lenas, et. al., "Adaptive Fuzzy Control of Mammalian Cell Culture in Fed-Batch Reactor for Production of an Antithrombin III Variant", Animal Cell Technology: Basic and Applied Aspects, 1998, vol. 9, pp. 217-221.
Levering, et al., "Physiology of myeloma cells grown in glucose-limited chemostat cultures", Cytotechnology, 1992, vol. 9, pp. 125-130.
Link, Thomas, "Glukoselimitierung als Strategie zur Steigerung der Produktion von MUC1 und anderen rekombinanten Glykoproteinen mit CHO-Zellen", Berichte des Forschungszentrums Jülich, Institut für Biotechnologie, Dissertation, Bonn University (175 pages) (In German with English abstract).
Linz, et. al., "Stoichiometry, Kinetics, and Regulation of Glucose and Amino Acid Metabolism of a Recombinant BHK Cell Line in Batch and Continuous Cultures", Biotechnol. Prog., 1997, vol. 13, pp. 453-463.
Lübben, Holger, "Diauxic Cell Behavior Enables Detoxification of CHO Cell Culture Medium During Fed Batch Cultivation", New Developments and New Applications in Animal Cell Technology, O.W. Marten, Kluwer Academic Publishers, 1998, pp. 267-271.
Lübben, Holger, Dissertation of the University of Hannover, Germany, 1997, pp. 1-157 (in German with English abstract).
Lüdemann, et. al., "Effects of NH3 on the cell growth of a hybridoma cell line", Cytotechnology, 1994, vol. 14, pp. 11-20.
Lüdemann, Fortschrittsberichte, VDI 17, Nr. 164, 1997, pp. 1-152 (In German).
Luli, et. al., "Comparison of Growth, Acetate Production and Acetate Inhibition of *Escherichia coli* Strains in Batch and Fed-Batch Fermentations", Applied and Environmental Microbiology, Apr. 1990. vol. 56, No. 4, pp. 1004-1011.
Michel-Savia, et al., "Control of the selectivity of butyric acid production and improvement of fermentation performance with *Clostridium tyrobutyricum*", Appl. Microbiol. Biotechnol., 1990, vol. 32, pp. 387-392.
Mizrahi, Avshelom, "Techniques and Equipment for Animal Cell Cultivation", European Society for Animal Cell Technology, 9th Meeting, 1988, pp. 314-321.
Niloperbowo, et. al., "Improved Monoclonal Antibody Production via Controlled Feeding Strategies During Fedbatch Cultures of Hybridoma Cell Line Utilizing Protein Free Media", Animal Cell Technology: Basic and Applied Aspects, S. Kaminogawa, et. al., Kluwer Academic Publishers, 1993, pp. 409-415.
Noll, et al., "Development of a metabolically optimized fermentation process based on a glucose-limited CHO perfusion culture", 18th Annual ESACT Meeting, May 11-15, 2003, Granada, Spain, abstract O-5.06, p. 75.
Oh, et. al., "Interactive Dual Control of Glucose and Glutamine Feeding in Hybridoma Cultivation", Journal of Fermentation and Bioengineering, 1996, vol. 81, No. 4, pp. 329-336.
Paalme, et al., "Glucose-Limited Fed-Batch Cultivation of *Escherichia coli* with Computer-Controlled Fixed Growth Rate", Biotechnolgy and Bioengineering, 1990, vol. 35, pp. 312-319.
Petrova, et. al., "Neural network modelling of fermentation processes. Microorganisms cultivation model", Bioprocess Engineering, 1997, vol. 16, pp. 145-159.
Petrova, et. al., "Neural network modelling of fermentation processes. Specific growth rate model", Bioprocess Engineering, 1998, vol. 18, pp. 281-287.
Pfaff, et. al., "Model-Aided On-Line Glucose Monitoring for Computer-Controlled High Cell Density Fermentation", Computer applications in biotechnology: a post print volume from the 6th International Conference, Garmisch-Paretenkirchen, Germany, A. Munack and K. Schügerl, Pergamon, 1995, pp. 6-11.
Pörtner, et. al., "High density fed-batch cultures for hybridoma cells performed with the aid of a kinetic model", Bioprocess Engineering, 1996, vol. 15, pp. 117-124.
Rose, et. al., "Mammalian Cell Culture: Process Development Considerations", Handbook of Industrial Cell Culture: Mammalian, Microbial and Plant Cells, Ch. 4, V.A. Vinci and S. R. Parakh, Humana Press, 2003, pp. 69-103.
Sanfeliu, et. al., "Identification of key patterns in the metabolism of hybridoma cells in culture", Enzyme and Microbiol. Technology, 1997, vol. 21, pp. 421-428.
Schubert, et. al., "Bioprocess optimization and control: Application of hybrid modelling", Journal of Biotechnology, 1994, vol. 33, pp. 51-68.
Schwabe, et. al., "Improving an on-line feeding strategy for batch-fed cultures of hybridoma cells by dialysis and 'Nutrient-Split'-feeding", Bioprocess Engineering, 1999, vol. 20, pp. 475-484.
Thermofisher Scientific, "Technical Resources: 11965—DMEM, high glucose", 2015, retrieved from http://www.thermofisher.com/us/en/home/technical-resources/media-formulation.8.html on Oct. 13, 2015 (2 pages).
Voet & Voet, Excerpts from "Biochemistry", Chapter 16-1, "The Glycolytic Pathway", 2nd edition, Nedah Rose, John Wiley and Sons, 1995, pp. 445, 464, 466.
Cruz, et. al., "Metabolically optimised BHK cell fed-batch cultures", J. Biotechnol., Jun. 2000, vol. 60, No. 2, pp. 109-118.
Ljunggren, et. al., "Catabolic control of hybridoma cells by glucose and glutamine limited fed batch cultures", Biotechnol. Bioeng., Sep. 1994, vol. 44, No. 7, pp. 808-818.
Arajuo, et .al., "Increased rheumatoid factor interference observed during immunogenicity assessment of an Fc-engineered therapeutic antibody", J. Pharm. Biomed. Analysis, 2001, vol. 55, pp. 1041-1049.
Bourdage, et. al., "Effect of double antigen bridging immunoassay format on antigen coating concentration dependence and implica-

(56) References Cited

OTHER PUBLICATIONS tions for designing immunogenicity assays for monoclonal antibodies", J. Pharmaceut. Biomed. Anal., 2005, vol. 39, pp. 685-690.
Eagle, Harry, "Amino Acid Metabolism in Mammalian Cell Cultures", Science, Aug. 1959, vol. 130, No. 3373, pp. 432-437.
Geng, et. al., "Validation of immunoassays used to assess immunogenicity to therapeutic monoclonal antibodies", J. Pharm. Biomed. Anal., 2005, vol. 39, pp. 364-375.
Ham, et. al., "Media and Growth Requirements", Methods in Enzymology, vol. LVIII, Jakoby and Pastan, Academic Press, New York, 1979, pp. 44-93.
Ham, Richard G., "Clonal Growth of Mammalian Cells in a Chemically Defined Synthetic Medium", Proc. Nat. Acad. Sci. U.S.A., Feb. 1965, vol. 53, No. 2, pp. 288-293.
Jayme, et. al., "Basal medium development for serum-free culture: a historical perspective", Cytotechnology, Jan. 1997, vol. 1, No. 3, pp. 95-101.
Kaliyaperumal, et. al., "Immunogenicity assessment of therapeutic proteins and peptides", Curr. Pharm. Biotechnol., 2010, vol. 10, pp. 352-358.
Mikulskis, et. al., "Solution ELISA as a platform of choice for development of robust, drug tolerant immunogenicity assays in support of drug development", J. Immunol. Methods, 2011, vol. 365, pp. 38-49.
Mire-Sluis et al., "Recommendations for the design and optimization of immunoassays used in the detection of host antibodies against biotechnology products," J. Immunol. Methods 2004, vol. 289, pp. 1-16.
Pan et al., "Comparison of the NIDS® rapid assay with ELISA methods in immunogenicity testing of two biotherapeutics," J. Pharmacolog. Toxicolog. Methods 2011, vol. 63, No. 2, pp. 150-159.
Pendley et al., "Bioanalytical interferences in immunoassays for antibody biotherapeutics," Bioanalysis 2011, vol. 3, No. 7, pp. 703-706.
Qiu et al. "A novel homogeneous Biotin-digoxigenin based assay for the detection of human anti-therapeutic antibodies in autoimmune serum," J. Immunol. Methods 2010, vol. 362, pp. 101-111.
Staack et al., "Quality requirements for critical assay reagents used in bioanalysis of therapeutic proteins: what bioanalysts should know about their reagents," Bioanalysis 2011, vol. 3, No. 5, pp. 523-534.
Stubenrauch et al., "Generic anti-drug antibody assay with drug tolerance in serum samples from mice exposed to human antibodies," Anal. Biochem. 2012, vol. 430, pp. 193-199.
Stubenrauch et al., "Subset analysis of patients experiencing clinical events of a potentially immunogenic nature in the pivotal clinical trials of tocilizumab for rheumatoid arthritis: Evaluation of an antidrug antibody ELISA using clinical adverse event-driven immunogenicity testing," Clin. Ther. 2010, vol. 32, No. 9, pp. 1597-1609.
Wurm, Florian M., "Production of recombinant protein therapeutics in cultivated mammalian cells", Nature Biotechnology, 2004, vol. 22, pp. 1393-1398.
Raju, T. Shantha, "Terminal sugars of Fc glycans influence antibody effector functions of IgGs," Current Opinion in Immunology, 2008, 20:471-478.
Hossler et al,. "Optimal and consistent protein glycosylation in mammalian cell culture," Glycobiology, 2009, 19(9):936-949.
Nyberg et al., "Metabolic Effects on Recombinant Interferon-γ Glycosylation in Continuous Culture of Chinese Hamster Ovary Cells," Biotechnol. Bioeng., Feb. 5, 1999, 62(3):336-347.
Kim et al., "Production of poly (3-hydroxybutyric-co-3-hydroxyvaleric acid) by fed-batch culture of *Alcaligenes eutrophus* with substrate control using on-line glucose analyzer," Enzyme and Microbial Technology, Jul. 1994, 16(7):556-561, Abstract.
Yuk, Inn Huam Yvonne, "Protein Expression and Glycosylation in CHO Cells," Thesis for Doctor of Philosophy in Chemical Engineering, Massachusetts Institute of Technology, 2001, 207 pages.

Cox et al., "Glycan optimization of a human monoclonal antibody in the aquatic plant *Lemna minor*," Nature Biotechnology, Dec. 2006, 24(12):1591-1597.
Van Berkel et al., "N-Linked Glycosylation is an Important Parameter for Optimal Selection of Cell Lines Producing Biopharmaceutical Human IgG," Biotechnol. Prog., 2009, 25:244-251.
Akerberg et al., "Modelling the influence of pH, temperature, glucose and lactic acid concentrations on the kinetics of lactic acid production by *Lactococcus lactis* ssp. *lactis* ATCC 19435 in whole-wheat flower," Applied Microbiology and Biotechnology, 1998, 49:682-690.
Ataai et al., "Simulation of the Growth Pattern of a Single Cell of *Escherichia coli* under Anaerobic Conditions," Biotechnology and Bioengineering, Jul. 1985, 27:1027-1035.
Barford et al., "Simulation of animal cell metabolism," Cytotechnology, 1992, 10:63-74.
Batt et al., "A Structured Kinetic Modeling Framework for the Dynamics of Hybridoma Growth and Monoclonal Antibody Production in Continuous Suspension Cultures," Biotechnology and Bioengineering, 1989, 34:515-531.
Batt et al., "Inclined Sedimentation for Selective Retention of Viable Hybridomas in a Continuous Suspension Bioreator," Biotechnol. Prog., 1990, 6:458-464.
Benthin et al., "Flow-injection analysis of micromolar concentrations of glucose and lactate in fermentation media," Analytica Chimica Acta, 1992, 261, 145-153.
Burgard et al., "Minimal Reaction Sets for *Escherichia coli* Metabolism under Different Growth Requirements and Uptake Environments," Biotechnology Progress, 2001, 17:791-797.
Butler et al., "Nutritional aspects of the growth of animal cells in culture," Journal of Biotechnology, 1989, 12:97-110.
Carlsson et al., "Fermentation Products and Bacterial Yields in Glucose-Limited and Nitrogen-Limited Cultures of Streptococci," Archives of Oral Biology, 1974, 19:1105-1109.
Cheng et al., "A Novel Feeding Strategy for Enhanced Plasmid Stability and Protein Production in Recombinant Yeast Fedbatch Fermentation," Biotechnology and Bioengineering, Oct. 5, 1997, 56(1):23-31.
Christopher et al., "Catabolic control of the enhanced alanine-preferring system for amino acid transport in glucose-starved hamster cells requires protein synthesis," Proc. Natl. Acad. Sci. USA, Apr. 1979, 76(4):1878-1881.
Cruz et al., "Metabolic responses to different glucose and glutamine levels in baby hamster kidney cell culture," Applied Microbiology and Biotechnology, 1999, 51:579-585.
De La Torre Sanchez, J.F., "Regulation of Glucose Metabolism in Bovine Embryos," 2004, Ph.D. Dissertation, Colorado State University, United States, retrieved Mar. 21, 2011 from Dissertation & Theses (Publication No. AAT 3143820), 191 pages.
Dean et al., "Continuous Cell Culture With Fluidized Sponge Beads," Large-Scale Cell Culture Technology, 1987, 145-167.
Doverskog et al., "Physiology of cultured animal cells," J. Biotechnol., 1997, 59:103-115.
Drosinos et al., "Production of acetate and lactate in relation to glucose content during modified atmosphere storage of gilt-head seabream (*Sparus aurata*) at 0 ± 1°C," Food Research International, 1997, 30(9):711-717.
Europa, Anna Lolita, "Control of Cell Metabolism and Multiplicity of Steady State in the Continuous Culture of Hybridoma Cells," Mar. 2001, Ph.D. Dissertation, University of Minnesota, United States, retrieved Mar. 22, 2011 from Dissertation & Theses (Publication No. AAT 3002794), 87 pages.
Frame et al., "Kinetic Study of Hybridoma Cell Growth in Continuous Culture. I. A Model for Non-Producing Cells," Biotechnology and Bioengineering, 1991, 37:55-64.
Fu et al., "Metabolic flux distributions in hybridoma cells at different metabolic states," Animal Cell Technology: Challenges for the 21st Century, Proceedings of the joint international meeting of the Japanese Association for Animal Cell Technology (JAACT) and the European Society for Animal Cell Technology (ESACT) 1998, Kyoto, Japan, Ikura et al., Eds., Kluwer Academic Publishers, Netherlands, 1999, 51-55.

(56) References Cited

OTHER PUBLICATIONS

Gambhir et al., "Analysis of Cellular Metabolism of Hybridoma Cells at Distinct Physiological States," Journal of Bioscience and Bioengineering, 2003, 95(4):317-327.
Gambhir et al., "Analysis of the use of fortified medium in continuous culture of mammalian cells," Cytotechnology, 1999, 31:243-254.
Gambhir, Anshu, "Analysis and Control of Mammalian Cell Metabolism at Multiple Steady States in Continuous Cultures," Nov. 1999, Ph.D. Dissertation, University of Minnesota, United States, retrieved Mar. 22, 2011 from Dissertation & Theses (Publication No. AAT 9950287), 239 pages.
Glacken et al., "Mathematical Descriptions of Hybridoma Culture Kinetics: I. Initial Metabolic Rates," Biotechnology and Bioengineering, 1988, 32:491-506.
Godia et al., "Cell Metabolism," Chapter 4, Cell Culture Technology for Pharmaceutical and Cell-Based Therapies, 2005, 81-112.
Ha et al., "Kinetics Analysis of Growth and Lactic Acid Production in pH-Controlled Batch Cultures of *Lactobacillus casei* KH-1 Using Yeast Extract/Corn Steep Liquor/Glucose Medium," Journal of Bioscience and Bioengineering, 2003, 96(2):134-140.
Hayter et al., "The Effect of the Dilution Rate on CHO Cell Physiology and Recombinant Interferon-γ Production in Glucose-Limited Chemostat Culture," Biotechnology and Bioengineering, 1993, 42:1077-1085.
Hirschel et al., "An Automated Hollow Fiber System for the Large Scale Manufacture of Mammalian Cell Secreted Product," in Lydersen, B.K., (ed.), Large Scale Cell Culture Technology, Hanser Publishers, N.Y., 1988, 113-144.
Honda et al., "Human Antithrombin III Variant Production from Recombinant BHK Cells in a Fed-Batch Culture with On-Line Control of Glucose and Glutamine Concentrations," Journal of Fermentation and Bioengineering, 1998, 85(5):532-535.
Hu et al., "Large-scale mammalian cell culture," Current Opinion in Biotechnology, 1997, 8:148-153.
Hu et al., "Monitoring and Control of Animal Cell Bioreactors: Biochemical Engineering Considerations," Large-Scale Mammalian Cell Culture Technology, Lubiniecki, Ed., Chapter 16, 1990, 451-481.
Huang et al., "On-line determination of glucose concentration throughout animal cell cultures based on chemiluminescent detection of hydrogen peroxide coupled with flow-injection analysis," Journal of Biotechnology, 1991, 81:161-172.
Jang et al., "Effect of the Macromolecular Metabolism of Murine Hybridoma Cells on Antibody Productivity in Batch and Fed-Batch Culture," Animal Cell Technology: Basic & Applied Aspects, Kitagawa et al., Eds., Kluwer Academic Publishers, Netherlands, 1999, vol. 10, 241-245.
Jang et al., "Enhancement of Antiboby Productivity in the Near-Zero Specific Growth Rate During Glucose and Glutamine-Limited Fed-Batch Culture of Hybridoma Cells," Animal Cell Technology: Challenges for the 21st Century, Proceedings of the joint international meeting of the Japanese Association for Animal Cell Technology, Ikura et al., Eds., Kluwer Academic Publishers, Netherlands, 1999, 75-79.
Johnston et al., "Industrial control of recombinant *E. coli* fed-batch culture: new perspectives on traditional controlled variables," Bioprocess and Biosystems Engineering, 2002, 25:111-120.
Kalyuzhnyi, S.V., "Batch anaerobic digestion of glucose and its mathematical modeling. II. Description, verification and application of model," Bioresource Technology, 1997, 59:249-258.
Kitano et al., "Production of human monoclonal antibodies by heterohybridomas," Appl. Microbiol. Biotechnol., 1986, 24:282-286.
Kurtanjek, Z., "Optimal Nonsingular Control of Fed-Batch Fermentation," Biotechnology and Bioengineering, Apr. 1991, 37:814-823.
Kyrolainen et al., "On-Line Calibration of a Computerized Biosensor System for Continuous Measurements of Glucose and Lactate," Biotechnology and Bioengineering, 1995, 45(2):122-128.

Lin et al., "Calorie restriction extends *Saccharomyces cerevisiae* lifespan by increasing respiration," Nature, 2002, 418:344-348.
Lin et al., "Modeling and Simulation of Lactic Acid Fermentation with Inhibition Effects of Lactic Acid and Glucose," Biotechnology and Bioprocess Engineering, Jul. 18, 2004, 9:52-58.
Ljunggren et al., "Glutamine limited fed-batch culture reduces the overflow metabolism of amino acids in myeloma cells," Cytotechnology, 1992, 8:45-56.
Macmillan et al., "Monoclonal Antibody Production in Stirred Reactors," Large-Scale Cell Culture Technology, 1987, 21-58.
Major, Nicholas Charles, "The Physiology of Lactic Acid Production by *Lactobacillus delbreuckii* in a Cell Recycle Fermenter," 1987, Ph.D. Dissertation, University of Kent at Canterbury (United Kingdom) retrieved Mar. 22, 2011 from Dissertation & Theses (Publication No. AAT DX80035), 228 pages.
Male et al., "On-Line Monitoring of Glucose in Mammalian Cell Culture Using a Flow Injection Analysis (FIA) Mediated Biosensor," Biotechnology and Bioengineering, Aug. 5, 1997, 55(3):497-504.
McKay et al., "High specific rates of glucose utilization under conditions of restricted growth are required for citric acid accumulation by *Yarrowia lipolytica* IMK 2," Applied Microbiology and Biotechnology, 1994, 41:73-78.
Mercier et al., "Kinetics of Lactic Acid Fermentation on Glucose and Corn by *Lactobacillus amylophilus*," Journal of Chemical Technology and Biotechnology, 1992, 55, 111-121.
Miller et al., "A Kinetic Analysis of Hybridoma Growth and Metabolism in Batch and Continuous Suspension Culture: Effect of Nutrient Concentration, Dilution Rate, and pH," Biotechnology and Bioengineering, 1988, 32:947-965 (Article Reprinted: Miller, W.M., et al., Biotechnol. Bioeng. 67 (2000) 853-871).
Miller et al., "Transient Responses of Hybridoma Cells to Nutrient Additions in Continuous Culture: I. Glucose Pulse and Step Changes," Biotechnology and Bioengineering, 1989, 33, 477-486.
Munyon et al., "The Relation Between Glucose Utilization, Lactic Acid Production and Utilization and the Growth Cycle of L Strain Fibroblasts," Experimental Cell Research, 1959, 17:490-498.
Naftalin, R.J., "Presteady-state uptake of glucose by the human erythrocyte is inconsistent with the mobile carrier model," Trends in Biochemical Sciences, Nov. 1988, 13, 425-426.
Newland et al., "Hybridoma growth limitations: The roles of energy metabolism and ammonia production," Cytotechnology, 1990, 3:215-229.
Oh et al., "Increased erythritol production in fed-batch cultures of *Torula* sp. by controlling glucose concentration," Journal of Industrial Microbiology & Biotechnology, 2001, 26, 248-252.
Ohleyer et al., "Continuous Production of Lactic Acid in a Cell Recycle Reactor," Applied Biochemistry and Biotechnology, 1985, 11, 317-332.
Ozturk et al., "Growth, Metabolic, and Antibody Production Kinetics of Hybridoma Cell Culture: 2. Effects of Serum Concentration, Dissolved Oxygen Concentration, and Medium pH in a Batch Reactor," Biotechnology Progress, 1991, 7:481-494.
Ozturk et al., "Real-Time Monitoring and Control of Glucose and Lactate Concentrations in a Mammalian Cell Perfusion Reactor," Biotechnology and Bioengineering, Feb. 20, 1997, 53(4), 372-378.
Ozturk, Sadettin S., "Cell Culture Technology—An Overview," Chapter 1, Cell Culture Technology for Pharmaceutical and Cell-Based Therapies, 2005, 1-40.
Patel et al., "The Lactate Issue Revisited: Novel Feeding Protocols to Examine Inhibition of Cell Proliferation and Glucose Metabolism in Hematopoietic Cell Cultures," Biotechnology Progress, 2000, 16, 885-892.
Petch et al., "Profile of Energy Metabolism in a Murine Hybridoma: Glucose and Glutamine Utilization," Journal of Cellular Physiology, 1994, 161, 71-76.
Pörtner et al., "Estimation of specific glucose uptake rates in cultures of hybridoma cells," Journal of Biotechnology, 1994, 34:237-246.
Ramirez et al., "Cell Cycle- and Growth Phase-Dependent Variations in Size Distribution, Antibody Productivity, and Oxygen Demand in Hybridoma Cultures," Biotechnology and Bioengineering, 1990, 36:839-848.

(56) References Cited

OTHER PUBLICATIONS

Reuveny et al., "Factors affecting cell growth and monoclonal antibody production in stirred reactors," J. Immunol. Methods, 1986, 86:53-59.
Robbins et al., "Optimization of *Escherichia coli* Growth by Controlled Addition of Glucose," Biotechnology and Bioengineering, 1989, 34:1289-1294.
Robinson et al., "Kinetics of Recombinant Immunoglobulin Production by Mammalian Cells in Continuous Culture," Biotechnology and Bioengineering, 1991, 38:972-976.
Rothen et al., "Glucose uptake kinetics of *Saccharomyces cerevisiae* monitored with a newly developed FIA," Journal of Biotechnology, 1996, 50:1-12.
Rupp et al., "Cellular Microencapsulation for Large-Scale Production of Monoclonal Antibodies," Large Scale Cell Culture Technology, Tolbert, W.R., Feder, J. (eds.) B.K. Lyndersen Hanser Publisher Munich, 1987, 82-93.
Schroeder et al., "Glucose Restriction and Refeeding Regimen Alters Proliferation and Differentiation of HC11 Mammary Cells," In Vitro Cellular & Development Biology—Animal, Mar. 2002, 38:135-136.
Schulz et al., "Real-time monitoring of lactate extrusion and glucose consumption of cultured cells using a lab-on-valve system," The Analyst, 2002, 127:1583-1588.
Schumpp et al., "Physiological studies on high cell density culture of different cell lines," Advances in Animal Cell Biology and Technology for Bioprocesses, 1989, 224-229.
Schwabe et al., "Improving an on-line feeding strategy for fed-batch cultures of hybridoma cells by dialysis and 'Nutrient-Split'-feeding," Bioprocess Engineering, 1999, 20:475-484.
Shah et al., "Utilization of Glucose and Amino Acids by *Bacteroides intermedius* and *Bacteroides gingivalis*," Current Microbiology, 1987, 15:241-246.
Shu et al., "A Mathematical Model for the Growth of a Single Cell of *E. coli* on a Glucose/Glutamine/Ammonium Medium," Biotechnology and Bioengineering, 1989, 33:1117-1126.
Siegwart et al., "Adaptive Control at Low Glucose Concentration of HEK-293 Cell Serum-Free Cultures," Biotechnol. Prog., 1999, 15:608-616.
Sinclair et al., "Amino Acid and Glucose Uptake in Relation to Protein Synthesis in Cells Growing in Tissue Culture," Biochimica et Biophysica Acta, 1959, 32:58-68.
Sivakesava et al., "Simultaneous determination of multiple components in lactic acid fermentation using FT-MIR, NIR, and FT-Raman spectroscopic techniques," Process Biochemistry, 2001, 37:371-378.
Sureshkumar et al., "The Influence of Temperature on a Mouse-Mouse Hybridoma Growth and Monoclonal Antibody Production," Biotechnology and Bioengineering, 1991, 37:292-295.
Takuma et al., "Effects of Glucose and $CO_2$ Concentrations on CHO Cell Physiology," Animal Cell Technology: Basic & Applied Aspects, Kluwer Academic Publishers, Netherlands, 2004, 13:99-103.
Tedesco, John L., "Analysis of Glucose and Lactic Acid in Cell Culture Media by Ion Moderated Partitioning High Performance Liquid Chromatography," Biotechniques, 1987, 5(1):46-51.
Thacker et al., "Effects of Food Restriction on Lactate Production from Glucose in Rat Isolated Adipocytes," Clinical Research, 1986, 34(1):198A.
Thacker et al., "Effects of food restriction on lactate production from glucose by rat adipocytes," American Journal of Physiology, 1987, 253(4 Part 1):E336-E342.
Tothill et al., "Monitoring of the glucose concentration during microbial fermentation using a novel mass-producible biosensor suitable for on-line use," Enzyme and Microbial Technology, 1997, 20, 590-596.
Tunner et al., "Use of Glucose Starvation to Limit Growth and Induce Protein Production in *Escherichia coli*," Biotechnology and Bioengineering, 1992, 40:271-279.
Tyler, Joseph E., "Microencapsulation of Mammalian Cells," Large-Scale Mammalian Cell Culture Technology, Lubiniecki, Ed., Marcel Dekker Inc., USA, 1990, 343-361.
van der Hoeven et al., "Growth of mixed cultures of *Actinomyces viscosus* and *Streptococcus mutans* under dual limitation of glucose and oxygen," FEMS Microbiology Letters, 1989, 62:275-284.
Wolfe et al., "Glucose Metabolism in the Calf Lens," Experimental Eye Research, 1985, 40:629-641.
Wolna et al., "Non-Steroidal Anti-Inflammatory Drugs: Effects on the Utilization of Glucose and Production of Lactic Acid in Tissue Culture," Cellular and Molecular Life Sciences, 1973, 29:69-71.
Xu et al., "Effects of Glucose and Lactic Acid on Insect Cell (Sf9) Culture," Chinese Journal of Biotechnology, 1996, 12:508-510.
Xu et al., "Raman measurement of glucose in bioreactor materials," SPIE, 1997, 2976:10-19.
Zeng, A.-P., "Quantitative assessment of cell density effect on the metabolism and antibody production rate of hybridoma cells at high cell density," Journal of Biotechnology, 1996, 45:243-251.
Zhang et al., "Application of mathematical models to the determination optimal glucose concentration and light intensity for mixotropic culture of *Spirulina platensis*," Process Biochemistry, 1999, 34:477-481.
Zhang et al., "Fed-batch culture of hybridoma cells in serum-free medium using an optimized feeding strategy," Journal of Chemical Technology & Biotechnology, 2004, 79:171-181.
Zhang et al., "Growth, Metabolism and Monoclonal Antibody Production of Hybridoma Cells in Glucose-limited Fed-batch Culture," Journal of East China University of Science and Technology, 2003, 29(5):476-479.
Technical Bulletin, SAFC Biosciences, Designing Feed Strategies for Fed-Batch CHO Cultures, issued Jul. 2008.
Wong, Y.H., Krishnaswamy, P.R., Teo, W.K. (1992) Biochemical Engineering for 2001, pp. 689-691.

\* cited by examiner

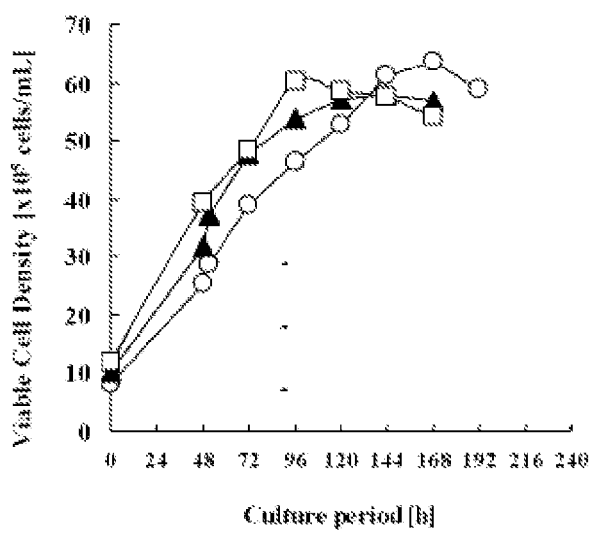
FIG._1A
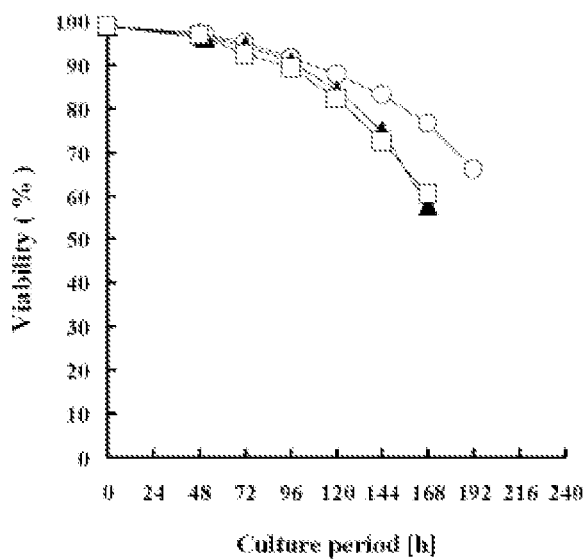
FIG._1B

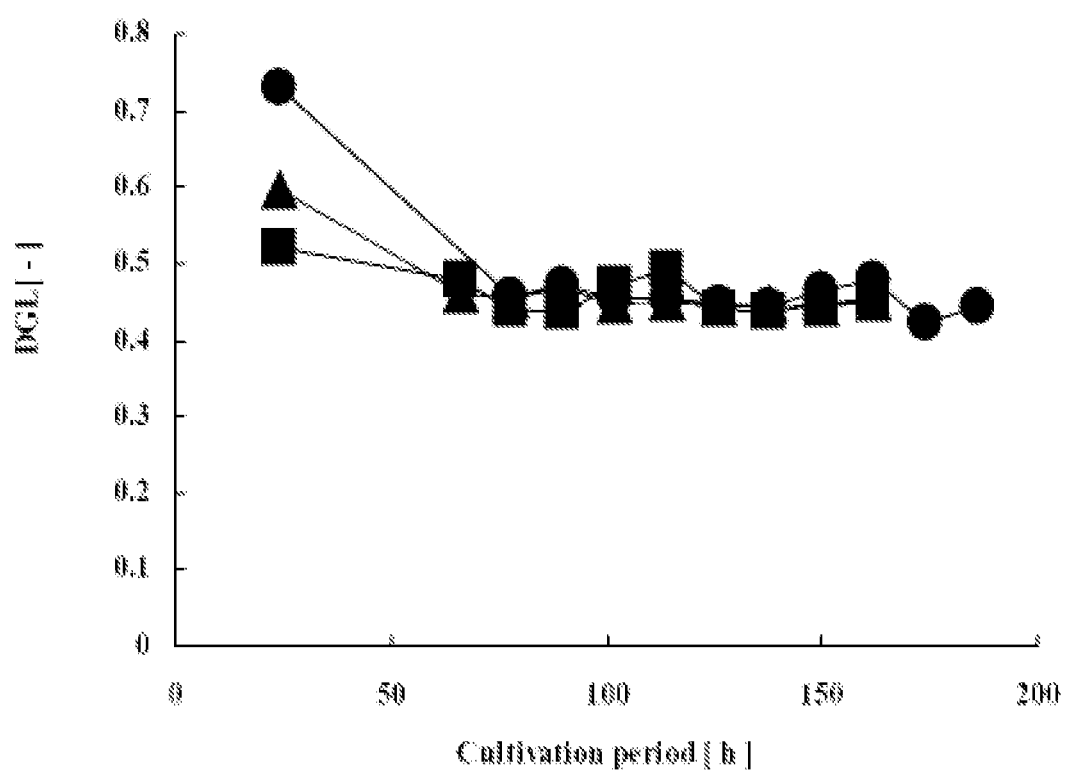
FIG._2

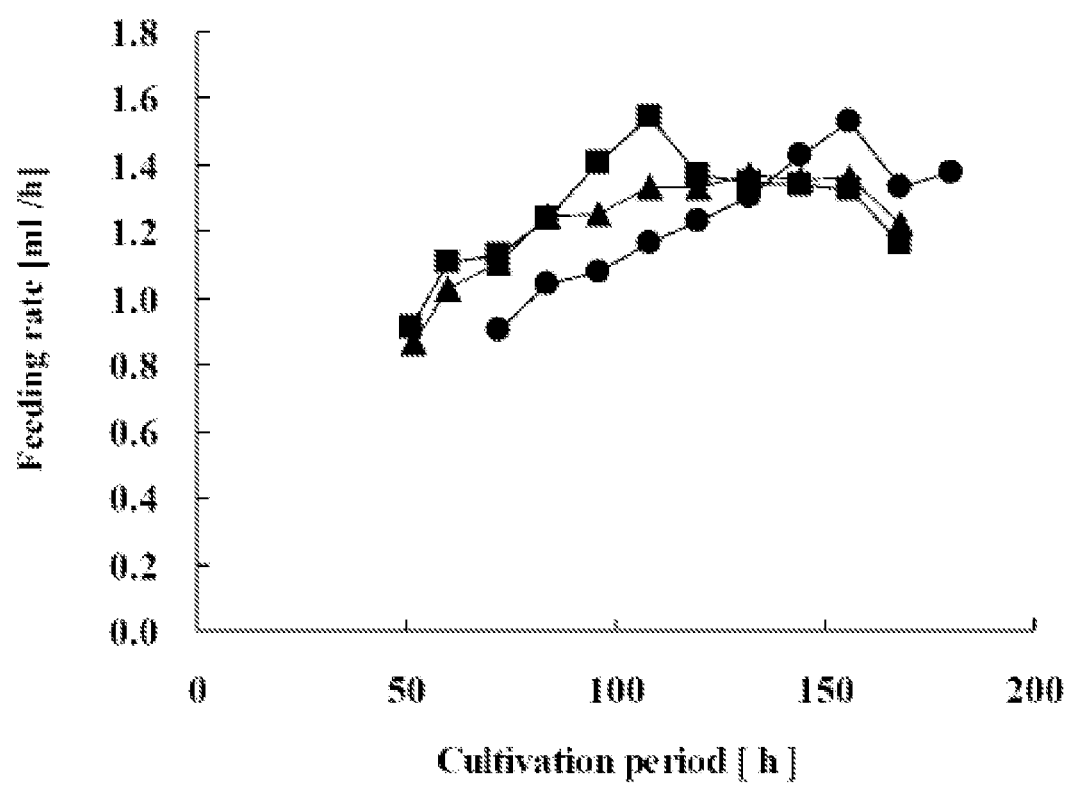
FIG._3

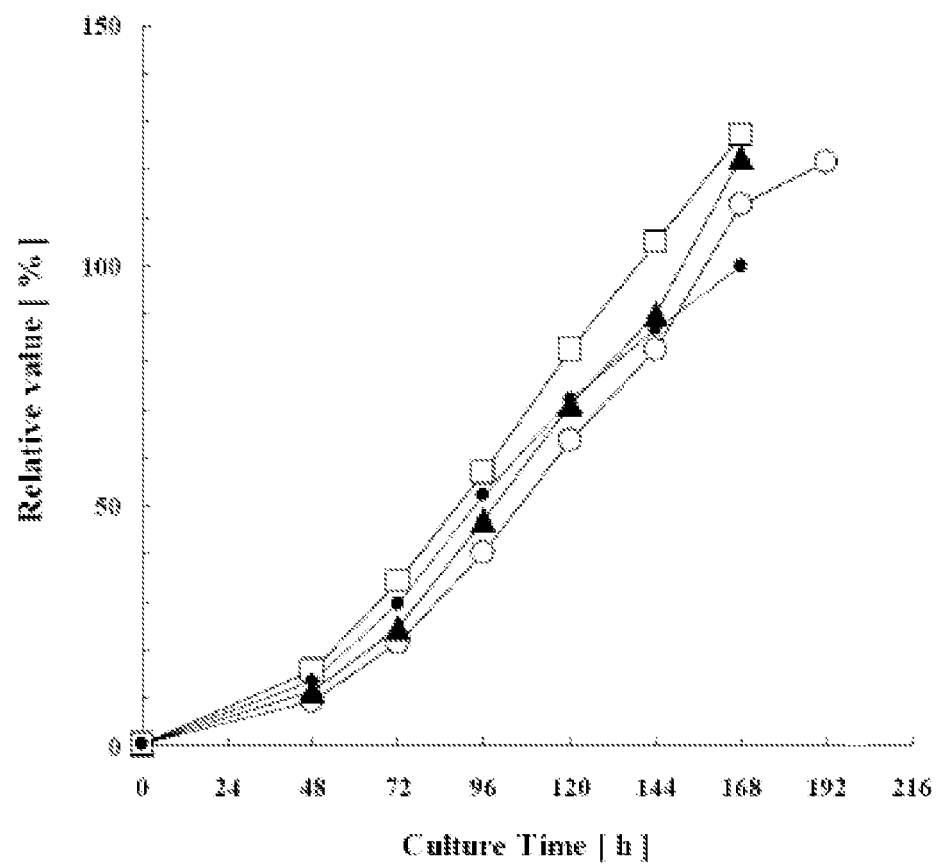
FIG._4

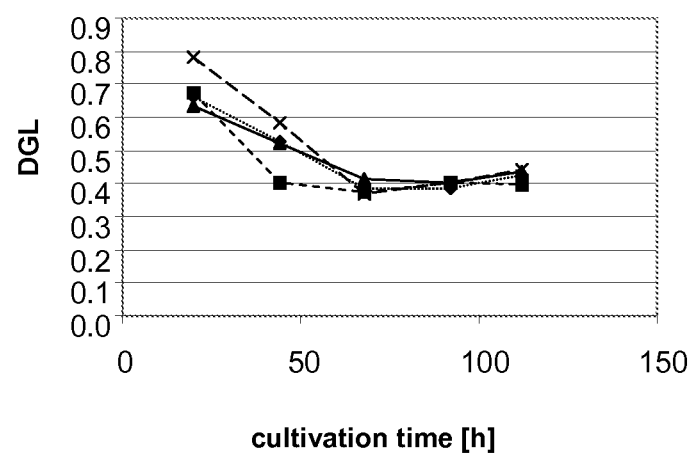
FIG._5

METHOD FOR THE PRODUCTION OF A GLYCOSYLATED IMMUNOGLOBULIN

RELATED APPLICATION

This is a continuation application which claims priority under 35 USC § 120 to non-provisional application Ser. No. 12/911,300, filed Oct. 25, 2010, which claims priority to European application no. 09013455.2 filed on Oct. 26, 2009, the contents of which are hereby incorporated by reference.

BACKGROUND OF THE INVENTION

Herein is reported a method in the field of immunoglobulin production in cells, whereby the glycosylation pattern of the produced immunoglobulin can be modified based on the cultivation conditions.

In recent years the production of immunoglobulins has steadily increased and it is likely that immunoglobulins will become the biggest group of therapeutics available for the treatment of various diseases in the near future. The impact of immunoglobulins emerges from their specificity, which comprises their specific target recognition and binding function as well as the activation of specific effects concurrently with or after antigen/Fc-receptor binding.

The specific target recognition and binding is mediated by the variable region of the immunoglobulin. Other parts of the immunoglobulin molecule, from which effects originate, are posttranslational modifications, such as the glycosylation pattern. The posttranslational modifications do have an influence on the efficacy, stability, immunogenic potential, binding etc. of an immunoglobulin. In connection therewith complement-dependent cytotoxicity (CDC), antibody-dependent cellular cytotoxicity (ADCC) and induction of apoptosis have to be addressed.

It has been reported that the glycosylation pattern of immunoglobulins, i.e. the saccharide composition and number of attached glycostructures, has a strong influence on the biological properties (see e.g. Jefferis, R., Biotechnol. Prog. 21 (2005) 11-16). Immunoglobulins produced by mammalian cells contain 2-3% by mass carbohydrates (Taniguchi, T., et al., Biochem. 24 (1985) 5551-5557). This is equivalent e.g. in an immunoglobulin of class G (IgG) to 2.3 oligosaccharide residues in an IgG of mouse origin (Mizuochi, T., et al., Arch. Biochem. Biophys. 257 (1987) 387-394) and to 2.8 oligosaccharide residues in an IgG of human origin (Parekh, R. B., et al., Nature 316 (1985) 452-457), whereof generally two are located in the Fc-region and the remaining in the variable region (Saba, J. A., et al., Anal. Biochem. 305 (2002) 16-31).

In the Fc-region of an immunoglobulin of class G oligosaccharide residues can be introduced via N-glycosylation at amino acid residue 297, which is an asparagine residue (denoted as $Asn^{297}$). Youings et al. have shown that a further N-glycosylation site exists in 15% to 20% of polyclonal IgG molecules in the Fab-region (Youings, A., et al., Biochem. J., 314 (1996) 621-630; see e.g. also Endo, T., et al., Mol. Immunol. 32 (1995) 931-940). Due to inhomogeneous, i.e. asymmetric, oligosaccharide processing, multiple isoforms of an immunoglobulin with different glycosylation pattern exist (Patel, T. P., et al., Biochem. J. 285 (1992) 839-845; Ip, C. C., et al., Arch. Biochem. Biophys. 308 (1994) 387-399; Lund, J., et al., Mol. Immunol. 30 (1993) 741-748). Concurrently the structure and distribution of the oligosaccharides is both highly reproducible (i.e. non-random) and site specific (Dwek, R. A., et al., J. Anat. 187 (1995) 279-292).

Some characteristics of an immunoglobulin are directly linked to the glycosylation of the Fc-region (see e.g. Dwek, R. A., et al., J. Anat. 187 (1995) 279-292; Lund, J., et al., J. Immunol. 157 (1996) 4963-4969; Lund, J., FASEB J. 9 (1995) 115-119; Wright, A. and Morrison, S. L., J. Immunol. 160 (1998) 3393-3402), such as for example thermal stability and solubility (West, C. M., Mol. Cell. Biochem. 72 (1986) 3-20), antigenicity (Turco, S. J., Arch. Biochem. Biophys. 205 (1980) 330-339), immunogenicity (Bradshaw, J. P., et al., Biochim. Biophys. Acta 847 (1985) 344-351; Feizi, T. and Childs, R. A., Biochem. J. 245 (1987) 1-11; Schauer, R., Adv. Exp. Med. Biol. 228 (1988) 47-72), clearance rate/circulatory half-life (Ashwell, G. and Harford, J., Ann. Rev. Biochem. 51 (1982) 531-554; McFarlane, I. G., Clin. Sci. 64 (1983) 127-135; Baenziger, J. U., Am. J. Path. 121 (1985) 382-391; Chan, V. T. and Wolf, G., Biochem. J. 247 (1987) 53-62; Wright, A., et al., Glycobiology 10 (2000) 1347-1355; Rifai, A., et al., J. Exp. Med. 191 (2000) 2171-2182; Zukier, L. S., et al., Cancer Res. 58 (1998) 3905-3908), and biological specific activity (Jefferis, R. and Lund, J., in Antibody Engineering, ed. by Capra, J. D., Chem. Immunol. Basel, Karger, 65 (1997) 111-128).

Factors influencing the glycosylation pattern have been investigated, such as for example presence of fetal calf serum in the fermentation medium (Gawlitzek, M., et al., J. Biotechnol. 42(2) (1995) 117-131), buffering conditions (Mülthing, J., et al., Biotechnol. Bioeng. 83 (2003) 321-334), dissolved oxygen concentration (Saba, J. A., et al., Anal. Biochem. 305 (2002) 16-31; Kunkel, J. P., et al., J. Biotechnol. 62 (1998) 55-71; Lin, A. A., et al., Biotechnol. Bioeng. 42 (1993) 339-350), position and conformation of the oligosaccharide as well as host cell type and cellular growth state (Hahn, T. J. and Goochee, C. F., J. Biol. Chem. 267 (1992) 23982-23987; Jenkins, N., et al., Nat. Biotechnol. 14 (1996) 975-981), cellular nucleotide-sugar metabolism (Hills, A. E., et al., Biotechnol. Bioeng. 75 (2001) 239-251), nutrient limitations (Gawlitzek, M., et al., Biotechnol. Bioeng. 46 (1995) 536-544; Hayter, P. M., et al., Biotechnol. Bioeng. 39 (1992) 327-335), especially glucose restriction (Tachibana, H., et al., Cytotechnology 16 (1994) 151-157), and extracellular pH (Borys, M. C., et al., Bio/Technology 11 (1993) 720-724).

Increased oligomannose structures as well as truncated oligosaccharide structures have been observed by the recombinant expression of immunoglobulins e.g. in NS0 myeloma cells (Ip, C. C., et al., Arch. Biochem. Biophys. 308 (1994) 387-399; Robinson, D. K., et al., Biotechnol. Bioeng. 44 (1994) 727-735). Under glucose starvation conditions variations in glycosylation, such as attachment of smaller precursor oligosaccharides or complete absence of oligosaccharide moieties, have been observed in CHO cells, Murine 3T3 cells, rat hepatoma cells, rat kidney cells and Murine myeloma cells (Rearick, J. I., et al., J. Biol. Chem. 256 (1981) 6255-6261; Davidson, S. K. and Hunt, L. A., J. Gen. Virol. 66 (1985) 1457-1468; Gershman, H. and Robbins, P. W., J. Biol. Chem. 256 (1981) 7774-7780; Baumann, H. and Jahreis, G. P., J. Biol. Chem. 258 (1983) 3942-3949; Strube, K.-H., et al., J. Biol. Chem. 263 (1988) 3762-3771; Stark, N. J. and Heath, E. C., Arch. Biochem. Biophys. 192 (1979) 599-609). A strategy based on low glutamine/glucose concentrations was reported by Wong, D. C. F., et al., Biotechnol. Bioeng. 89 (2005) 164-177.

The Japanese Patent Application JP 62-258252 reports a perfusion culture of mammalian cells, whereas U.S. Pat. No. 5,443,968 reports a fed-batch culture method for protein secreting cells. In WO 98/41611 a method for cultivating cells is reported effective to adapt the cells to a metabolic state characterized by low lactate production. A method for culturing cells in order to produce substances is reported in WO 2004/048556. Elbein, A. D., Ann. Rev. Biochem. 56 (1987) 497-534, reports that mammalian cells when incubated in the absence of glucose transfer mannose-5 containing structures instead of mannose-9 containing structures to proteins. The dependence of pCO2 influences during glucose limitation on CHO cell growth, metabolism and IgG production is reported by Takuma, S., et al. in Biotechnol. Bioeng. 97 (2007) 1479-1488.

SUMMARY OF THE INVENTION

It has been found that the amount of the mannose-5 glycostructure in the glycosylation pattern of a polypeptide produced by a eukaryotic cell can be modified based on the amount of glucose provided to the cell in the cultivation process. By reducing the amount of glucose available, e.g. by changing the DGL value from 1.0 to smaller values of e.g. 0.8, 0.6, 0.5, 0.4, or 0.2, a modification in the mannose-5 glycostructure amount in the glycosylation pattern can be obtained. The DGL value or respectively the amount of glucose available per time unit has to be kept constant and at a defined reduced value per time unit.

A first aspect as reported herein is a method for the production of a polypeptide, in one embodiment of an immunoglobulin, in a eukaryotic cell, comprising the following steps
   a) providing a eukaryotic cell comprising a nucleic acid encoding the polypeptide,
   b) cultivating the cell under conditions wherein the degree of glucose limitation (DGL) is kept constant and wherein the DGL is less than 0.8, and
   c) recovering the polypeptide from the culture,
wherein the fraction of the polypeptide with a mannose-5 glycostructure is 10% or less of the sum comprising the amount of the polypeptide with a mannose-5 glycostructure, the amount of the polypeptide G(0) isoform, the amount of the polypeptide G(1) isoform, and the amount of the polypeptide G(2) isoform.

In one embodiment the DGL is kept constant in the range from 0.8 to 0.2. In a further embodiment the DGL is kept constant in the range from 0.6 to 0.4. In another embodiment the fraction of the polypeptide with a mannose-5 glycostructure is 8% or less of the sum comprising the polypeptide with a mannose-5 glycostructure, the polypeptide G(0) isoform, the polypeptide G(1) isoform, and the polypeptide G(2) isoform. In still another embodiment the polypeptide is an immunoglobulin, in one embodiment an immunoglobulin of class G or E.

Another aspect as reported herein is a method for the production of an immunoglobulin comprising the following steps:
   a) providing a mammalian cell comprising a nucleic acid encoding the immunoglobulin,
   b) cultivating the cell in a cultivation medium wherein the amount of glucose available in the cultivation medium per time unit is kept constant and limited to less than 80% of the amount that could maximally be utilized by the cells in the cultivation medium per time unit, and
   c) recovering the immunoglobulin from the cells or the cultivation medium.

In one embodiment the amount of glucose available in the cultivation medium per time unit is kept constant and limited to a value in the range from 80% to 20%. In a further embodiment the range is from 60% to 40%. In another embodiment the cells in the cultivation medium are the viable cells in the cultivation medium.

In one embodiment of the aspects as reported herein the eukaryotic cell is selected from CHO cells, NS0 cells, HEK cells, BHK cells, hybridoma cells, PER.C6® cells, insect cells, or Sp2/0 cells. In one embodiment the eukaryotic cell is a Chinese Hamster Ovary (CHO) cell. In another embodiment of the aspects as reported herein the cultivating is at a pH value in the range from about pH 7.0 to about pH 7.2.

In still another embodiment of the aspects as reported herein the cultivating is a continuous or a fed-batch cultivating. The methods may comprise in another embodiment a final step of purifying the polypeptide. In still another embodiment the cell is cultivated for six to twenty days or for six to fifteen days. In a further embodiment the cell is cultivated for six to eight days.

Another aspect as reported herein is a composition comprising an immunoglobulin, wherein the composition has been prepared with a method as reported herein.

In one embodiment the immunoglobulin is an anti-IL-6R antibody. In a further embodiment the anti-IL-6R antibody comprises Tocilizumab. In another embodiment the mannose-5 glycostructure attached to the anti-IL-6R antibody is 8% or less. In still a further embodiment the mannose-5 glycostructure is 6% or less. In another embodiment the mannose-5 glycostructure is 4% or less.

The invention also concerns a composition comprising an antibody that binds human interleukin 6 receptor (anti-IL-6R antibody) with oligosaccharide attached thereto, wherein mannose-5 glycostructure (M5) content in the composition is 8% or less, e.g. less than 5%, for example, 4% or less. In one embodiment, the anti-IL-6R antibody is Tocilizumab and/or has been produced by a recombinant Chinese Hamster Ovary (CHO) cell.

BRIEF DESCRIPTION OF THE DRAWINGS

FIGS. 1A and 1B Viable cell density (FIG. 1A) and cell viability profiles (FIG. 1B) in the fed-batch mode using the DGL control; open circle: initial cell density of $8 \times 10^5$ cells/ml; filled triangle: initial cell density of $10 \times 10^5$ cells/ml; open square: initial cell density of $12 \times 10^5$ cells/ml.

FIG. 2 Time courses of DGL in the fed-batch mode in immunoglobulin production; circle: initial cell density of $8 \times 10^5$ cells/ml; triangle: initial cell density of $10 \times 10^5$ cells/ml; square: initial cell density of $12 \times 10^5$ cells/ml.

FIG. 3 Feeding profiles based on DGL by the fed-batch mode in immunoglobulin production; circles: initial cell density of $8 \times 10^5$ cells/ml; triangle: initial cell density of $10 \times 10^5$ cells/ml; square: initial cell density of $12 \times 10^5$ cells/ml.

FIG. 4 Immunoglobulin production profiles by the fed-batch mode in the DGL control; open circles: initial cell density of $8 \times 10^5$ cells/ml; filled triangle: initial cell density of $10 \times 10^5$ cells/ml; open square: initial cell density of $12 \times 10^5$ cells/ml; filled small circle: constant feeding method: FR=0.02 g glucose/h (control)

FIG. 5 Time curse of DGL during a fed-batch cultivation of a cell: diamond: single feed daily feeding, square: dual feed daily feeding; triangle: single feed profile feeding; X: dual feed profile feeding.

DETAILED DESCRIPTION OF THE INVENTION

Herein is reported a method for the production of an immunoglobulin comprising the following steps:
a) cultivating a mammalian cell comprising a nucleic acid encoding the immunoglobulin in a cultivation medium at a constant DGL of less than 0.8 (i.e. the amount of glucose available per time unit is constant and 80% or less of the amount of glucose that can maximally be utilized by the cell per time unit), and
b) recovering the immunoglobulin from the cells or the culture medium.

With the method as reported herein an immunoglobulin can be obtained wherein the amount of the immunoglobulin with a mannose-5 glycostructure depends on the adjusted DGL value, and wherein the amount is the fraction of the sum of the amount of the immunoglobulin with a mannose-5 glycostructure, and of the immunoglobulin G(0) isoform, and of the immunoglobulin G(1) isoform, and of the immunoglobulin G(2) isoform. In one embodiment the DGL is from 0.8 to 0.2. In this embodiment the fraction is 10% or less. In another embodiment the DGL is from 0.6 to 0.4. In this embodiment the fraction is 6% or less. With the method as reported herein an immunoglobulin can be obtained wherein the fraction of the immunoglobulin having a mannose-5 glycostructure is 10% or less of the sum comprising the amount of the immunoglobulin with a mannose-5 glycostructure, the amount of the immunoglobulin G(0) isoform, the amount of the immunoglobulin G(1) isoform, and the amount of the immunoglobulin G(2) isoform. In another embodiment the fraction is the area-% fraction determined in a liquid chromatography method. In one embodiment the DGL is maintained in the range from 0.8 to 0.2. In another embodiment the DGL is maintained in the range from 0.6 to 0.2. In still another embodiment the DGL is maintained in the range from 0.6 to 0.4. In one embodiment the amount of glucose that can maximally be utilized by the cell per time unit is the average amount of glucose that is utilized in a cultivation in which all compounds are available in excess, i.e. no compound is limiting the growth of the cell, determined based on at least five cultivations. In one embodiment the fraction is determined on day seven of the cultivation.

Methods and techniques known to a person skilled in the art, which are useful for carrying out the current invention, are described e.g. in Ausubel, F. M. (ed.), Current Protocols in Molecular Biology, Volumes I to III (1997), Wiley and Sons; Sambrook, J., et al., Molecular Cloning: A Laboratory Manual, Third Edition, Cold Spring Harbor Laboratory Press, Cold Spring Harbor, N.Y. (2001); Glover, N. D. (ed.), DNA Cloning: A Practical Approach, Volumes I and II (1985); Freshney, R. I. (ed.), Animal Cell Culture (1986); Miller, J. H. and Calos, M. P. (eds.), Gene Transfer Vectors for Mammalian Cells, Cold Spring Harbor Laboratory Press, Cold Spring Harbor, N.Y. (1987); Watson, J. D., et al., Recombinant DNA, Second Edition, N.Y., W.H. Freeman and Co (1992); Winnacker, E. L., From Genes to Clones, N.Y., VCH Publishers (1987); Celis, J. (ed.), Cell Biology, Second Edition, Academic Press (1998); Freshney, R. I., Culture of Animal Cells: A Manual of Basic Techniques, Second Edition, Alan R. Liss, Inc., N.Y. (1987).

The use of recombinant DNA technology enables the production of numerous derivatives of a polypeptide. Such derivatives can, for example, be modified in individual or several amino acid positions by substitution, alteration or exchange. The derivatization can, for example, be carried out by means of site directed mutagenesis. Such variations can easily be carried out by a person skilled in the art (Sambrook, J., et al., Molecular Cloning: A laboratory manual, Third Edition (2001) Cold Spring Harbor Laboratory Press, New York, USA; Hames, B. D. and Higgins, S. G., Nucleic acid hybridization—a practical approach (1985) IRL Press, Oxford, England).

The term "nucleic acid" denotes a naturally occurring or partially or fully non-naturally occurring nucleic acid molecule encoding a polypeptide. The nucleic acid can be build up of DNA-fragments which are either isolated or synthesized by chemical means. The nucleic acid can be integrated into another nucleic acid, e.g. in an expression plasmid or the genome/chromosome of a eukaryotic cell. The term "plasmid" includes shuttle and expression plasmids. Typically, the plasmid will also comprise a prokaryotic propagation unit comprising an origin of replication (e.g. the ColE1 origin of replication) and a selectable marker (e.g. ampicillin or tetracycline resistance gene), for replication and selection, respectively, of the plasmid in prokaryotic cells. To a person skilled in the art procedures and methods are well known to convert an amino acid sequence, e.g. of a polypeptide, into a corresponding nucleic acid encoding the respective amino acid sequence. Therefore, a nucleic acid is characterized by its nucleic acid sequence consisting of individual nucleotides and likewise by the amino acid sequence of a polypeptide encoded thereby.

The term "expression cassette" denotes a nucleic acid that contains the elements necessary for expression and optionally for secretion of at least the contained structural gene in/from a cell, such as a promoter, polyadenylation site, and 3'- and 5'-untranslated regions.

The term "gene" denotes e.g. a segment on a chromosome or on a plasmid, which is necessary for the expression of a polypeptide. Beside the coding region a gene comprises other functional elements including a promoter, introns, and one or more transcription terminators. A "structural gene" denotes the coding region of a gene without a signal sequence.

The term "expression" denotes the transcription and translation of a structural gene within a cell. The level of transcription of a structural gene in a cell can be determined on the basis of the amount of corresponding mRNA that is present in the cell. For example, mRNA transcribed from a selected nucleic acid can be quantitated by PCR or by Northern hybridization (see e.g. Sambrook et al. (supra)). A polypeptide encoded by a nucleic acid can be quantitated by various methods, e.g. by ELISA, by determining the biological activity of the polypeptide, or by employing methods that are independent of such activity, such as Western blotting or radioimmunoassay, using antibodies that recognize and bind to the polypeptide (see e.g. Sambrook et al. (supra)).

The term "cell" denotes a cell into which a nucleic acid encoding a polypeptide, in one embodiment a heterologous polypeptide, has been introduced. The term "cell" includes both prokaryotic cells used for propagation of plasmids/vectors as well as eukaryotic cells used for expression of the structural gene. In one embodiment a eukaryotic cell for the expression of an immunoglobulin is a mammalian cell. In another embodiment the mammalian cell is selected from CHO cells, NS0 cells, Sp2/0 cells, COS cells, HEK cells, BHK cells, PER.C6® cells, and hybridoma cells. A eukaryotic cell can be selected in addition from insect cells, such as caterpillar cells (*Spodoptera frugiperda*, sf cells), fruit fly cells (*Drosophila melanogaster*), mosquito cells (*Aedes aegypti, Aedes albopictus*), and silkworm cells (*Bombyx Mori*), and the like.

The term "polypeptide" denotes a polymer of amino acid residues joined by peptide bonds, whether produced naturally or synthetically. Polypeptides of less than about 20 amino acid residues may be referred to as "peptides". Polypeptides of more than 100 amino acid residues or covalent and non-covalent aggregates comprising more than one polypeptide may be referred to as "proteins". Polypeptides may comprise non-amino acid components, such as carbohydrate groups. The non-amino acid components may be added to the polypeptide by the cell in which the polypeptide is produced, and may vary with the type of cell. Polypeptides are defined herein in terms of their amino acid sequence in N- to C-terminal direction. Additions thereto, such as carbohydrate groups, are generally not specified, but may be present nonetheless.

The term "heterologous DNA" or "heterologous polypeptide" denotes a DNA molecule or a polypeptide, or a population of DNA molecules or a population of polypeptides, which do not exist naturally within a given cell. DNA molecules heterologous to a particular cell may contain DNA derived from the cell's species (i.e. endogenous DNA) so long as that DNA is combined with non-host DNA (i.e. exogenous DNA). For example, a DNA molecule containing a non-cell's DNA segment, e.g. encoding a polypeptide, operably linked to a cell's DNA segment, e.g. comprising a promoter, is considered to be a heterologous DNA molecule. Likewise, a heterologous DNA molecule can comprise an endogenous structural gene operably linked to an exogenous promoter. A polypeptide encoded by a heterologous DNA molecule is a "heterologous" polypeptide.

The term "expression plasmid" denotes a nucleic acid comprising at least one structural gene encoding a polypeptide to be expressed. Typically, an expression plasmid comprises a prokaryotic plasmid propagation unit, including an origin of replication and a selection marker, e.g. for $E.\ coli$, an eukaryotic selection marker, and one or more expression cassettes for the expression of the structural gene(s) of interest each in turn comprising a promoter, at least one structural gene, and a transcription terminator including a polyadenylation signal. Gene expression is usually placed under the control of a promoter, and such a structural gene is to be "operably linked to" the promoter. Similarly, a regulatory element and a core promoter are operably linked if the regulatory element modulates the activity of the core promoter.

The term "isolated polypeptide" denotes a polypeptide that is essentially free from associated cellular components, such as carbohydrate, lipid, or other proteinaceous or non-proteinaceous impurities, which are not covalently associated with the polypeptide. Typically, a preparation of an isolated polypeptide contains in certain embodiments the polypeptide in a highly purified form, i.e. at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate polyacrylamide gel electrophoresis (SDS-page) of the preparation and Coomassie Brilliant Blue staining of the gel. However, the term "isolated" does not exclude the presence of the same polypeptide in alternative physical forms, such as dimers, or alternatively glycosylated or derivatized forms.

Immunoglobulins in general are assigned into five different classes: IgA (immunoglobulin of class A), IgD, IgE, IgG and IgM. Between these classes the immunoglobulins differ in their overall structure and/or amino acid sequence but have the same building blocks. Complete immunoglobulins are built up of two pairs of polypeptide chains, each comprising an immunoglobulin light polypeptide chain (short: light chain) and an immunoglobulin heavy polypeptide chain (short: heavy chain). In turn the chains comprise a variable region and a constant region. In a light chain both regions consist of one domain, whereas in a heavy chain the variable region consists of one domain and the constant region comprises up to five domains (in N- to C-terminal direction): the $C_H1$-domain, optionally the hinge region domain, the $C_H2$-domain, the $C_H3$-domain, and optionally the $C_H4$-domain. An immunoglobulin can be dissected in a Fab- and an Fc-region. The entire light chain, the heavy chain variable domain and the $C_H1$ domain are referred to as Fab-region (fragment antigen binding-region). The Fc-region comprises the $C_H2$-, $C_H3$-, and optionally the $C_H4$-domain.

As used herein, the term "immunoglobulin" denotes a protein consisting of one or more polypeptides. The encoding immunoglobulin genes include the different constant region genes as well as the myriad immunoglobulin variable region genes. The term "immunoglobulin" comprise in one embodiment monoclonal antibodies and fragments thereof, such as an isolated heavy chain, or a heavy chain constant region, as well as fusion polypeptides comprising at least an immunoglobulin heavy chain $C_H2$-domain. In one embodiment of the method as reported herein the immunoglobulin is a complete immunoglobulin, in another embodiment the immunoglobulin is an Fc-region of a complete immunoglobulin. In another embodiment the immunoglobulin is an immunoglobulin, or an immunoglobulin fragment, or an immunoglobulin conjugate.

The term "immunoglobulin fragment" denotes a polypeptide comprising at least the $C_H2$-domain of an immunoglobulin delta, epsilon, or alpha heavy chain, and/or the $C_H3$-domain of an immunoglobulin epsilon or delta heavy chain. Encompassed are also derivatives and variants thereof wherein the N-glycosylation motif Asn-Xaa-Ser/Thr in the $C_H2$- or $C_H3$-domain is not changed.

The term "immunoglobulin conjugate" denotes a polypeptide comprising at least the $C_H2$-domain of an immunoglobulin delta, epsilon, or alpha heavy chain, and/or the $C_H3$-domain of an immunoglobulin epsilon or delta heavy chain fused to a non-immunoglobulin polypeptide. Therein the N-glycosylation motif Asn-Xaa-Ser/Thr in the $C_H2$- or $C_H3$-domain is not changed.

The oligosaccharides attached to $Asn^{297}$ (IgG, IgE) or $Asn^{263}$ (IgA) of a $C_H2$-domain and/or to $Asn^{394}$, $Asn^{445}$, or $Asn^{496}$ (IgE, IgD) of a $C_H3$-domain of an immunoglobulin heavy chain have a biantennary structure (Mizuochi, T., et al., Arch. Biochem. Biophys. 257 (1987) 387-394), i.e. they consist of a core structure of

Man($\alpha$1-4)GlcNAc($\beta$1-4)GlcNAc→Asn with an optional Fuc($\alpha$1-6) linkage at the terminal GlcNAc residue. Two outer-arms are connected to the terminal mannose of the core structure having the formula

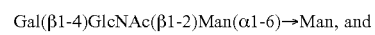

Gal($\beta$1-4)GlcNAc($\beta$1-2)Man($\alpha$1-6)→Man, and

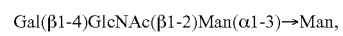

Gal($\beta$1-4)GlcNAc($\beta$1-2)Man($\alpha$1-3)→Man, wherein the terminal galactose residues are optional (Man=mannose, GlcNAc=N-acetyl glucose, Gal=galactose; Fuc=fucose).

TABLE 1

Glycosylation sites of immunoglobulins.

| immunoglobulin class | residue to which a glycostructure can be attached |
|---|---|
| IgG | Asn 297 |
| IgE | Asn 255, Asn 297, Asn 361, Asn 371, Asn 394 |
| IgA | Asn 263, Asn 459 |
| IgD | Asn 445, Asn 496 |
| IgM | Asn 395 |

The term "the amount of the immunoglobulin G(0) isoform, the amount of the immunoglobulin G(1) isoform, and the amount of the immunoglobulin G(2) isoform" denotes the sum of the amounts of the different, heterogeneous, biantennary oligosaccharides N-linked to an asparagine (Asn) of an immunoglobulin. The G(2) isoform has a terminal galactose residue on each of the outer-arms of the oligosaccharide structure, the G(1) isoform bears only a galactose residue on either the (α1-6) or (α1-3) linked outer-arm, and the G(0) isoform bears no galactose residue on both outer-arms.

The term "mannose-5 glycostructure" denotes an oligomannose-structure linked to an Asn residue of a polypeptide comprising or consisting of five mannose residues and two N-acetyl glucose core residues, forming a triantennary structure.

One aspect as reported herein is a method for the production of an immunoglobulin comprising the following steps:
a) cultivating a eukaryotic cell, preferably a mammalian cell, comprising one or more nucleic acid(s) encoding the immunoglobulin in a cultivation medium wherein the amount of glucose available in the cultivation medium per time unit is kept constant and limited to a value of less than 80% of the amount that could maximally be utilized by the eukaryotic cells in the cultivating per time unit, and
b) recovering the immunoglobulin from the cell or the culture medium and thereby producing an immunoglobulin.

With this method an immunoglobulin is obtained comprising at most 10% of an immunoglobulin with a mannose-5 glycostructure. The 10% are calculated based on the sum of the amount of the immunoglobulin with a mannose-5 glycostructure, the amount of the immunoglobulin G(0) isoform, the amount of the immunoglobulin G(1) isoform, and the amount of the immunoglobulin G(2) isoform.

The terms "degree of glucose limitation" and its abbreviation "DGL", which can be used interchangeably herein, denote the ratio of the current specific glucose consumption rate of a single cell in a cultivation to the maximum known specific glucose consumption rate of the single cell or a single cell of the same kind. The degree of glucose limitation is defined as $$DGL = \frac{qGlc}{qGlc_{max}}$$

with qGlc=current specific glucose consumption rate of a single cell;
$qGlc_{max}$=maximum known specific glucose consumption rate for this single cell or a single cell of the same kind.

The DGL can vary between $DGL_{maintenance}$ and 1 whereby $DGL_{maintenance}$ (<1 and >0) denotes complete growth limitation and 1 denotes no limitation or complete glucose excess.

The introduction of glycostructures to polypeptides, e.g. immunoglobulins, is a post-translational modification. Due to incompleteness of the glycosylation procedure of the respective cell every expressed polypeptide is obtained with a glycosylation pattern comprising different glycostructures. Thus, a polypeptide is obtained from a cell expressing it in form of a composition comprising differently glycosylated forms of the same polypeptide, i.e. with the same amino acid sequence. The sum of the individual glycostructures is denoted as glycosylation pattern, comprising e.g. polypeptides with completely missing glycostructures, differently processed glycostructures, and/or differently composed glycostructures.

One glycostructure is the mannose-5 glycostructure (also denoted as high-mannose, Man5, M5, or oligo-mannose). It has been reported, that the fraction of recombinantly produced polypeptides with the mannose-5 glycostructure is increased with prolonged cultivation time or under glucose starvation conditions (Robinson, D. K., et al., Biotechnol. Bioeng. 44 (1994) 727-735; Elbein, A. D., Ann. Rev. Biochem. 56 (1987) 497-534).

It has been found that the amount of the mannose-5 glycostructure in the glycosylation pattern of a polypeptide produced by a eukaryotic cell can be modified based on the amount of glucose provided to the cell in the cultivation process. It has been found that by reducing the amount of glucose, i.e. by changing the DGL value from 1.0 to smaller values of e.g. 0.8, 0.6, 0.5, 0.4, or 0.2, a modification in the mannose-5 glycostructure amount in the glycosylation pattern can be achieved. In one embodiment the DGL value is kept constant at a value within a range, such as from 0.8 to 0.2, or from 0.6 to 0.4. That is, the production of a polypeptide, in one embodiment of an immunoglobulin, can be performed under conditions wherein a restricted amount of glucose is available to the cultivated cell in order to obtain the polypeptide with a defined amount of the mannose-5 glycostructure in the glycosylation pattern. It has been found that a cultivation with an amount of glucose available per time unit of 80% or less of the amount of glucose that can maximally be utilized by the cells per time unit, in one embodiment by exponentially growing cells, i.e with a DGL of 0.8 or less, yields a polypeptide with a glycosylation pattern in which the amount of the mannose-5 glycostructure is changed compared to a cultivation with a DGL of 1.0. In one embodiment the cell density is the viable cell density. Additionally the obtained polypeptide yield is increased.

The term "the amount of glucose that can maximally be utilized by the cell per time unit" denotes the amount of glucose that is maximally consumed or utilized or metabolized per time unit by a single cell under optimum growth conditions in the exponential growth phase in a cultivation without any nutrient limitation. Thus, the amount of glucose that can maximally be utilized by the cell per time unit can be determined by determining the amount of glucose that is metabolized per time unit by a cell under optimum growth conditions in the exponential growth phase in a cultivation without any nutrient limitation. A further increase of the available amount of glucose will not further increase, i.e. change, the amount of glucose that can maximally be utilized by the cell per time unit. This amount defines the maximum level of glucose consumption of a single cell. This does not denote that a genetically modified version of the cell might not have an even higher maximum level of glucose consumption. Alternatively the amount of glucose that can be maximally be utilized by the cell per time unit can be determined based on previous cultivations and the monitored data.

The process as reported herein is particularly simple to carry out, associated with a minimum effort for measuring and control, and particularly economic.

Without restrictions, e.g. insufficient nutrient supply, cultivated cells grow and consume nutrients at maximum rates in an uneconomic manner. One of the consumed culture medium nutrients is glucose, which is metabolized by the cultivated cells in order to produce energy and building blocks for the cell's metabolism. In the presence of excess glucose the cell's metabolism is running at the maximum turnover rate for glucose. The amount of glucose that can maximally be utilized by the cell per time unit can for example be determined from the glucose consumption of exponentially growing cells in the presence of excess glucose cultivated with or under the same cultivation conditions that will also be used in the cultivation with restricted glucose, i.e. with an amount of glucose available per time unit that is smaller than that which can be utilized by the cell. This maximum amount can be calculated easily by determining the cell density and glucose concentration at the beginning and end of a fixed time range. The value is normally in a range from 0.006 to 190 mmol/hour/$10^9$ cells (Baker, K. N., et al., Biotechnol. Bioeng. 73 (2001) 188-202; WO 98/41611; Müthing, J., et al., Biotechnol. Bioeng. 83 (2003) 321-334; WO 2004/048556). In one embodiment the $qGlc_{max}$ is about 0.142 mmol/hour/$10^9$ cells under standard process conditions at pH 7.0.

The method as reported herein is performed in one embodiment under conditions wherein the amount of glucose available per time unit is kept constant and at 80% or less of the amount of glucose that can maximally be utilized by the cell per time unit (0.8≥DGL>0), in one embodiment the amount of glucose available is kept constant and at 60% or less (0.6≥DGL>0), in another embodiment at 50% or less (0.5≥DGL>0), and in still another embodiment at about 40%. The term "about" as used within this application denotes that the value is no exact value it is merely the central point of a range wherein the value can vary up to 10%, i.e. the term "about 40%" denotes a range from 44% to 36% (DGL=0.44–0.36).

In one embodiment the cultivating is with an amount of glucose available per time unit that is kept constant in a range between 80% and 10% of the amount of glucose that can maximally be utilized by the cell per time unit (0.8≥DGL≥0.1). In another embodiment the amount of glucose available is kept constant in a range between 60% and 10% (0.6≥DGL≥0.1). In a further embodiment the amount of glucose available is kept constant in a range between 50% and 10% (0.5≥DGL≥0.1). In another embodiment the amount of glucose available is kept constant in a range between 45% and 20% (0.45≥DGL≥0.2). In also an embodiment the amount of glucose available is kept between 80% and 60% (0.8≥DGL≥0.6).

In one embodiment the method comprises the step of cultivating the cell under conditions wherein the DGL is kept constant and at a value of about 0.4, whereby the cultivating comprises starting with a DGL between 1.0 and 0.5, lowering the DGL to a value of about 0.4, and keeping the DGL constant thereafter. In one embodiment the lowering of the DGL is within a time period of 100 hours. The term "keeping the DGL constant" and grammatical equivalents thereof denote that the DGL value is maintained during a time period, i.e. the variation of the DGL value is within 10% of the value (see e.g. FIG. 2).

The immunoglobulin is recovered after production, either directly or after disintegration of the cell. The recovered immunoglobulin is in one embodiment purified with a method known to a person skilled in the art. Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

For example, a purification process for immunoglobulins in general comprises a multistep chromatographic part. In the first step non-immunoglobulin polypeptides are separated from the immunoglobulin fraction by an affinity chromatography, e.g. with protein A or G. Afterwards, e.g., ion exchange chromatography can be performed to disunite the individual immunoglobulin classes and to remove traces of protein A, which has been coeluted from the first column. Finally a chromatographic step is employed to separate immunoglobulin monomers from multimers and fragments of the same class.

General chromatographic methods and their use are known to a person skilled in the art. See for example, Chromatography, $5^{th}$ edition, Part A: Fundamentals and Techniques, Heftmann, E. (ed.), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F. and Poole, S. K., Elsevier Science Publishing Company, New York, (1991); Scopes, R. K., Protein Purification: Principles and Practice (1982); Sambrook, J., et al. (ed.), Molecular Cloning: A Laboratory Manual, Third Edition, Cold Spring Harbor Laboratory Press, Cold Spring Harbor, N.Y., 2001; or Current Protocols in Molecular Biology, Ausubel, F. M., et al. (eds), John Wiley & Sons, Inc., New York (1990).

In one embodiment the recovered immunoglobulin is characterized by the amount of the immunoglobulin having a mannose-5 glycostructure with respect to the amount of a population, which is the sum of the amount of the immunoglobulin with a mannose-5 glycostructure, the immunoglobulin G(0) isoform, the immunoglobulin G(1) isoform, and the immunoglobulin G(2) isoform. With the method as reported herein the amount of the immunoglobulin with a mannose-5 glycostructure is in one embodiment 10% or less of the population, in another embodiment 8% or less of the population, and in a further embodiment 6% or less of the population.

The method as reported herein can be performed in certain embodiments as continuous cultivation, as fed-batch cultivation, or as combination thereof, e.g. starting as fed-batch cultivation with subsequent crossover to a continuous cultivation. Additionally, the method as reported herein can be performed in different ways. For example, in one embodiment prior to the cultivating under conditions with a DGL value below 1.0, i.e. for example under conditions wherein the available amount of glucose is 80% or less of the amount of glucose that can maximally be utilized by the cell in the culture per time unit, the cultivating is with an excess of glucose, i.e. a DGL value of 1.0. In another embodiment the cultivating is started with an amount of glucose as contained in standard culture media, e.g. between 1 and 10 g/l culture medium, e.g. in order to obtain a predefined cell density, e.g. in one embodiment of $10^5$ cell/ml. In a further embodiment the starting of the cultivating is in the presence of an excess amount of glucose, i.e. a DGL of 1.0, and adding an amount of glucose per time unit, which is 80% or less of the amount of glucose that can maximally be utilized per time unit by the cells in the cultivation. In another embodiment the feeding is started once the amount of glucose present in the culture medium has dropped to or below a preset value in the cultivation. In the last two cases the amount of glucose available in the culture is reduced by the metabolism of the cells in the cultivation.

In one embodiment the amount of glucose, which is available or added per time unit and which is less than the amount of glucose that can maximally be utilized, is kept at the same value, i.e. constant, in the method as reported herein. For example, if an amount of 50% of the amount of glucose that can maximally be utilized per time unit is available, this amount is available in all time units of the method in which a restricted glucose feeding is performed. It has to be pointed out that this value is a relative value. Though, as the viable cell density changes during the cultivation (i.e. it increases in the beginning, reaches a maximum, and drops thereafter again) the absolute amount of available glucose changes accordingly as it is a relative value depending on the absolute viable cell density. As the relative value is kept constant (i.e. at e.g. 80%) but the absolute reference value changes (i.e. e.g. increasing viable cell density) also the relative absolute value changes (i.e. 80% of an increasing value are also increasing).

The term "per time unit" denotes a fixed time range, such as 1 minute, 1 hour, 6 hours, 12 hours, or 24 hours. In one embodiment the time unit is 12 hours or 24 hours. The term "amount of glucose available per time unit" as used within this application denotes the sum of 1) the amount of glucose contained in the cultivation medium of a cultivation at the beginning of a fixed time range and 2) the amount of glucose added, i.e. fed, during the time unit. Thus, an amount of glucose is added to the cell cultivation medium, e.g. to the cultivation vessel, which increases the amount of glucose in the cultivation medium at the beginning of the fixed time range to the predetermined amount. This amount of glucose can be added, e.g., as solid, dissolved in water, dissolved in a buffer, or dissolved in a nutrient medium, whereby water and buffer shall not contain glucose. The amount of glucose to be added corresponds to the amount of glucose to be available reduced by the amount of glucose present in the medium in the cultivation vessel. The process of adding the amount of glucose can be performed either as single addition, as multiple addition of small, equal fractions, or as continuous addition during a time unit as described above.

The method as reported herein is suitable for any kind of cultivation and any cultivation scale. For example, in one embodiment the method is used for continuous or fed-batch processes; in another embodiment the cultivation volume is from 100 ml up to 50,000 l, in another embodiment from 100 l to 10,000 l. The method as reported herein is useful for the production of immunoglobulins with 10% or less, or 8% or less, or 6% or less of the immunoglobulin having a mannose-5 glycostructure. In one embodiment the immunoglobulin is an immunoglobulin G or E. The method as reported herein comprises a eukaryotic cell, wherein the cell in turn comprises a nucleic acid encoding the heavy chain of an immunoglobulin or a fragment thereof and a nucleic acid encoding the light chain of an immunoglobulin or a fragment thereof. The eukaryotic cell is in one embodiment selected from CHO cells, NS0 cells, BHK cells, hybridoma cells, PER.C6® cells, Sp2/0 cells, HEK cells, and insect cells.

A person skilled in that art is familiar with medium compositions and components as well as nutrient concentrations required by different cells for optimal growth in addition to the amount of glucose and will choose an appropriate medium for the cultivation of the cell (see e.g. Mather, J. P., et al. in Encyclopedia of Bioprocess Technology: Fermentation, Biocatalysis, and Bioseparation, Vol. 2 (1999) 777-785).

In one embodiment the amount of glucose that has to be available to the cells in a cultivation according to the method as reported herein is calculated by multiplying the viable cell density, which can be achieved normally in the culture vessel at a certain point of time of the cultivation, with the volume of the culture vessel and the amount of glucose that can maximally be utilized by the exponentially growing cells per time unit and by the intended DGL. In more detail, from the course of the glucose concentration in the cultivation and the course of the cell density in the cultivation prior to the actual point of time the future course of the glucose concentration and the cell density are predicted. With this prediction the amount of glucose that has to be added to the cultivation to achieve the intended DGL is calculated with the following formula:

$$\text{(glucose to be added } [pg \text{ glucose/ml/h}]) = \\ \text{(current cell density [cells/ml])} \times \text{(maximum glucose consumption} \\ \text{rate of the cell } [pg \text{ glucose/cell/h}]) \times (DGL \text{ value}) - \\ \text{amount of glucose present in the medium in the cultivation vessel.}$$

In one embodiment the pH value of the cultivation is between pH 6.5 and pH 7.8. In another embodiment the pH value is between pH 6.9 and pH 7.3. In a further embodiment the pH value is between pH 7.0 and pH 7.2. It has been found as outlined in Example 1 that in combination with a restricted glucose feeding with a pH value of 7.0 in the constant feeding method the M5 content can efficiently be regulated to defined values, i.e. below 8%, compared to a pH value of 7.2. In the cultivations in the fed-batch method at pH values of 7.0 or 7.2, respectively, it was found that with the DGL control method the M5 content could be regulated to be less than 5.5%. It has been found that with a reduction of the pH value of the cultivation an increase of the M5 amount due to the lowering of the DGL value can be traversed.

The cultivation is in one embodiment performed at a temperature between 27° C. and 39° C., in another embodiment between 35° C. and 37.5° C.

With the method as reported herein any polypeptide containing a glycostructure can be produced, such as immunoglobulins, interferons, cytokines, growth factors, hormones, plasminogen activator, erythropoietin and the like.

The cultivating in the method as reported herein can be performed using any stirred or shaken culture devices for mammalian cell cultivation, for example, a fermenter type tank cultivation device, an air lift type cultivation device, a culture flask type cultivation device, a spinner flask type cultivation device, a microcarrier type cultivation device, a fluidized bed type cultivation device, a hollow fiber type cultivation device, a roller bottle type cultivation device, or a packed bed type cultivation device.

The method as reported herein is performed in one embodiment for up to 15 days. In another embodiment the cultivating is for 6 to 15 days. In one embodiment the immunoglobulin is an anti-IL-6R antibody.

The method as reported herein is exemplified with an antibody to human interleukin-6 receptor as reported e.g. in EP 0 409 607, EP 0 628 639, U.S. Pat. No. 5,670,373, or 5,795,965 (herewith incorporated by reference in their entirety) as this antibody and the cell line expressing it were available at sufficient quantity in our laboratory at the time of the invention. This is not intended to restrict the scope of the invention.

The following examples and figures are available to aid the understanding of the present invention, the true scope of which is set forth in the appended claims. It is understood that modifications can be made in the procedures set forth without departing from the spirit of the invention.

EXAMPLES

Materials and Methods

Cell Line:

An exemplary CHO cell line in which the amount of the mannose-5 glycostructure of a recombinantly produced immunoglobulin can be modified is a CHO cell line comprising a nucleic acid encoding an anti-IL-6 receptor antibody according to EP 0 409 607 and U.S. Pat. No. 5,795,965. For the cultivation of the recombinant CHO cell any culture medium can be used as long a glucose supplementation according to the method of the invention can be performed. Exemplary culture media are IMDM, DMEM or Ham's F12 medium or combinations thereof, which have been adapted to the method as reported herein in as much as the mass ratios of the culture medium components to glucose are adopted. It is likewise possible to exclude glucose from the cultivation medium and add it to the cultivation separately.

Cultivation:

CHO cells expressing an anti-IL-6R antibody were cultivated in a 1l or 2l fermentation vessel. The feeding medium contained 15 to 40 g/l glucose. Glucose could be fed with a separate concentrated solution containing of e.g. 400 g/l glucose. The cultivation was performed at a pH value of in the range from pH 7.0 to pH 7.2.

Determination of the Glycostructure:

For the analysis of IgG glycosylation pattern a method according to Kondo et al. (Kondo, A., et al., Agric. Biol. Chem. 54 (1990) 2169-2170) was used. The IgG was purified from the centrifuged supernatant of the cultivation medium using a small scale protein A column. The oligosaccharide of the purified IgG was released using N-glycosidase F (Roche Diagnostics GmbH, Mannheim, Germany) and labeled with 2-amino pyridine at the reducing terminus. The labeled oligosaccharide was analyzed by reverse-phase chromatography (HPLC). Each peak was assigned by both mass spectrometry and standards for the oligosaccharides.

Glucose Determination:

The glucose concentration was determined using an YSI 2700 SELECT™ analyzer (YSI, Yellow Springs, Ohio, USA) with a method according to the manufacturer's manual.

Viable Cell Density Determination:

Viable Cell density was determined using an automatic image processing and analysis system (CEDEX®; Innovatis, Germany) and the trypan blue dye-exclusion method.

Example 1

Effects of the DGL Control and pH on Antibody Production and Mannose-5 Glycostructure (M5) Content A test was conducted using a CHO cell strain producing humanized anti-human IL-6 receptor antibody (Tocilizumab, RoACTEMRA®)), which was prepared in accordance with the method described in Referential Example 2 of Japanese Unexamined Patent Publication No. 99902/1996 by use of human elongation factor 1αpromotor as reported in Example 10 of International Patent Application Publication No. WO 92/19759 (corresponding to U.S. Pat. Nos. 5,795,965, 5,817,790, and 7,479,543).

In the constant absolute amount feeding method, effects of pH control on immunoglobulin production were observed. Table 2 shows the effects of pH control on antibody oligosaccharides production and M5 content in constant feeding mode.

TABLE 2

Effects of pH control in constant absolute amount feeding mode.

| No. | Sample on [day] | pH set-point | DGL | Relative antibody concentration [%] | M5 content [%] |
|---|---|---|---|---|---|
| 1 | 7 | 7.0 | 0.80-0.45 | 90.1 | 3.6 |
| 2 | 7 | 7.0 | 0.49-0.21 | 100 | 5.4 |
| 3 | 7 | 7.2 | 0.73-0.35 | 135.1 | 11.7 |
| 4 | 7 | 7.2 | 0.69-0.30 | 120 | 10.8 |
| 5 | 7 | 7.2 | 0.35-0.29 | 127 | 25.2 |
| 6 | 7 | 7.2 | 0.64-0.25 | 122.5 | 8.7 |

At pH 7.0 the amount of the mannose-5 glycostructure (M5) was regulated to less than 5.5%. The DGL value declined from 0.80 to 0.21 due to the change of cell density. On the other hand, at pH 7.2, the M5 amount fluctuated between 8.7% and 25.2% and was higher than that at pH 7.0. The DGL value at pH 7.2 varied from 0.73 to 0.25. Moreover, in this case, immunoglobulin production at pH 7.2 was more than 120% (relative value compared to pH 7.0). Higher immunoglobulin production in the constant absolute amount feeding method induces a higher M5 content of more than 8%. Therefore, with a pH 7.0 control in the constant absolute amount feeding method the M5 content could efficiently be regulated to lower values, i.e. below 8%, compared to pH 7.2 control method.

The DGL control method (=constant relative amount feeding method) was also used for the immunoglobulin production by fed-batch mode at various pH values, and the M5 content was analyzed. Table 3 shows the effects of DGL control after the start of feeding at day 2-3 and pH on immunoglobulin production and M5 content.

TABLE 3

Effects of DGL and pH control in fed-batch mode.

| No. | Sample on [day] | pH set-point | DGL | Relative antibody concentration [%] | M5 content [%] |
|---|---|---|---|---|---|
| 1 | 7 | 7.0 | 0.8 | 102.7 | 2.9 |
| 2 | 7 | 7.0 | 0.6 | 96.2 | 2.7 |
| 3 | 7 | 7.0 | 0.4 | 100.0 | 3.3 |
| 4 | 7 | 7.0 | 0.3 | 91.1 | 3.9 |

TABLE 3-continued

Effects of DGL and pH control in fed-batch mode.

| No. | Sample on [day] | pH set-point | DGL | Relative antibody concentration [%] | M5 content [%] |
|---|---|---|---|---|---|
| 5 | 7 | 7.0 | 0.2 | 83.0 | 4.0 |
| 6 | 7 | 7.2 | 0.6 | 100.9 | 4.4 |
| 7 | 7 | 7.2 | 0.4 | 90.1 | 5.3 |

At pH 7.0 the DGL control method was applied in the range of a DGL from 0.2 to 0.8. As a result, the M5 content was regulated to be equal or less than 4.0%. On the other hand, at pH 7.2, the DGL value was operated in the range from 0.4 to 0.6. Here the M5 content could be controlled to be less than 5.5%.

Example 2

Cultivating with Different DGL Values

The cultivating of a CHO cell comprising a nucleic acid encoding an anti-IL-6R antibody was performed with different DGL values. The results are summarized in the following Table 4.

TABLE 4

Effects of DGL control value on immunoglobulin production and M5 content.

| No. | Sample on [day] | DGL | Relative antibody concentration [%] | M5 content [%] | G(0) content [%] | G(1) content [%] | G(2) content [%] |
|---|---|---|---|---|---|---|---|
| 1 | 7 | 0.6-0.5 | 107.3 | 3.5 | 38.4 | 46.7 | 11.4 |
| 2 | 7 | 0.4 | 111.0 | 3.5 | 38.8 | 46.9 | 10.8 |
| 3 | 7 | 0.2 | 111.5 | 4.5 | 40.1 | 45.2 | 10.1 |
| 4 | 8 | const. feeding | 100.0 | 5.9 | 43.8 | 42.0 | 8.3 |

Compared to a constant feeding shows the controlled DGL strategy with a DGL value of 0.4 to 0.6 a reduced mannose-5 content.

Example 3

Cultivating with Different Feeding Strategies

The cultivating of a CHO cell comprising a nucleic acid encoding an anti-IL-6R antibody was performed with one DGL value but with different feeding strategies. The results are summarized in the following Table 5.

TABLE 5

Effects of feed strategy on viability and viable cell density.

| No. | Sample after [h] | DGL | feeding | adjustment | viability [%] | viable cell density [×10⁶ cells/ml] |
|---|---|---|---|---|---|---|
| 1 | 112 | 0.4 | single | daily | 71 | 5.1 |
| 2 | 115 | 0.4 | dual | daily | 75 | 5.8 |
| 3 | 115 | 0.4 | single | profile | 73 | 4.9 |
| 4 | 115 | 0.4 | dual | profile | 70 | 5.1 |

In the single feed experiments a single feed was used containing all nutrients and glucose. In the dual feed experiments two feeds were used: the first feed contains all nutrients and glucose at a low concentration of 15 g/l and the second feed contains a high concentration of glucose. These different feed experiments were performed in one set with a daily adjustment of the feeding rate and in another set following a predetermined profile based on the viable cell density development recorder in earlier cultivations. As can be seen from Table 5 viability and viable cell density are comparable independently of the employed feeding strategy.

Example 4

Degree of Glucose Limitation (DGL) Control for Immunoglobulin Production by the Fed-Batch Mode CHO cells ($8.0-12 \times 10^5$ cells/ml) were inoculated in serum free culture media as described above. The cells were grown at 37° C., 98% relative humidity, and 10% $CO_2$ atmosphere. In the fed-batch cultivation the feeding medium containing glucose was started to be fed to the main fermenter on the $2^{nd}$ or $3^{rd}$ day from the beginning of the cultivation. The feeding strategy followed the method to control the degree of glucose limitation (DGL) according to U.S. Patent Application Publication No. US 2006/0127975 A1. The DGL can be defined as the ratio of the observed specific glucose consumption rate to the maximum known specific glucose consumption rate when glucose is freely available for these cells ($DGL=Q(glc)/Q(glc)_{max}$, where $Q(glc)$=currently observed specific glucose consumption rate; $Q(glc)_{max}$=maximum known specific glucose consumption rate for these cells).

FIG. 1 shows the viable cell density and cell viability profiles of the cultivation. The DGL was controlled to be at a value of 0.4-0.5 in various cell densities as shown in FIG. 2. The feeding rates were changed once or twice a day depending on the cell density at that time. FIG. 3 shows the feeding profiles based on DGL by the fed-batch mode. The feeding rate was changed between 0.8 and 1.6 ml/h depending on the cell density. With this feeding strategy applied, an immunoglobulin production profile was obtained as shown in FIG. 4. Using the inoculation size of $10 \times 10^5$ cells/ml and $12 \times 10^5$ cells/ml, the immunoglobulin production was almost the same and more than 120% of the immunoglobulin production in constant feeding method at day seven as shown in Table 6 (feeding rate of 0.02 g glucose/h). In spite of the 20% difference in the initial cell densities, it was possible with the DGL control method to obtain approximately equivalent immunoglobulin titer. Moreover, when the inoculation size was set at $8.0 \times 10^5$ cells/ml, despite the 20 hour delay of the feeding start point, the immunoglobulin obtained was more than 110% (relative value) at day seven. In these results, the DGL control method could achieve a stable immunoglobulin production at various inoculation sizes.

Example 5

The Effects of the DGL Control on the Mannose-5 Glycostructure and Galactosylation of Oligosaccharides Of the immunoglobulin produced by fed-batch cultivation using the DGL control the glycosylation pattern was analyzed. Table 6 shows the result of the oligosaccharide analysis for the immunoglobulin obtained from the DGL controlled fed-batch cultivation in comparison with the constant feeding method (feeding rate: 0.02 g of glucose/h). At the inoculation size of $8.0 \times 10^5$ cells/ml, the content of mannose-5 glycostructure (M5) was 2.8%. At the inoculation size of $10 \times 10^5$ cells/ml and $12 \times 10^5$ cells/ml, the M5 content was 4.1% and 3.8%, respectively. At all cultivation conditions, the DGL control method was able to regulate the M5 content to less than 5.0%.

Meanwhile, in each condition, immunoglobulin G(0) isoform and immunoglobulin G(2) isoform were controlled at the range from 40% to 46% and from 9.0% to 11%, respectively.

TABLE 6

Effects of DGL control value on immunoglobulin production and glycosylation pattern.

| No | Sample on [day] | DGL | inoculation cell density [×10⁵ cells/ml] | relative antibody concentration [%] | M5 conten [%] | G(0) content [%] | G(1) content [%] | G(2) content [%] |
|---|---|---|---|---|---|---|---|---|
| 1 | 7 | constant feeding | 10 | 100.0 | 3.5 | 45.7 | 41.5 | 9.2 |
| 2 | 7 | 0.4 | 8 | 112.5 | 2.8 | 41.7 | 44.7 | 10.8 |
| 3 | 7 | 0.4 | 10 | 122.6 | 4.1 | 42.9 | 43.1 | 9.8 |
| 4 | 7 | 0.4 | 12 | 127.1 | 3.8 | 45.5 | 41.5 | 9.1 |

What is claimed:

1. A method for the production of an immunoglobulin comprising
   a) cultivating a Chinese Hamster Ovary (CHO) cell comprising a nucleic acid encoding the immunoglobulin in a cultivation medium with restricted glucose feeding wherein the amount of glucose available in the cultivation medium per time unit is kept constant in all time units in which restricted glucose feeding is performed and the degree of glucose limitation (DGL) is limited to a single constant value in a range between 0.5 and 0.1, wherein feeding is started once the amount of glucose present in the cultivation medium has dropped to or below a preset value in the cultivation and wherein said cultivation is a fed-batch cultivating, and
   b) recovering the immunoglobulin.

2. The method according to claim 1, wherein the restricted glucose feeding is started at day 2 or day 3 of the cultivating.

3. The method according to claim 1, wherein the cultivating is at a pH value from pH 6.5 to 7.5.

4. The method according to claim 3, wherein the cultivating is at a pH value from pH 6.9 to 7.3.

5. The method according to claim 4, wherein the cultivating is at a pH value from pH 6.95 to pH 7.05 or at a pH value from pH 7.15 to pH 7.25.

6. The method according to claim 1, wherein the immunoglobulin is an immunoglobulin of class G or class E.

7. The method according to claim 1, wherein cultivating the CHO cell is performed for six to twenty days.

8. The method according to claim 1, wherein the immunoglobulin is an anti-IL-6R antibody.

9. The method according to claim 1, wherein the DGL is limited to a constant value in a range between 0.45 and 0.2.

10. The method according to claim 1, wherein the DGL is limited to 0.4, or 0.2.

11. The method according to claim 8, wherein the anti-IL-6R antibody comprises tocilizumab.

12. The method according to claim 8, wherein the DGL is limited to a constant value in a range between 0.45 and 0.2.

13. The method according to claim 8, wherein the DGL is limited to 0.4, or 0.2.

14. The method according to claim 11, wherein the DGL is limited to a constant value in a range between 0.45 and 0.2.

15. The method according to claim 11, wherein the DGL is limited to 0.4, or 0.2.

16. The method according to claim 1, wherein the fraction of the immunoglobulin with a mannose-5 glycostructure is 10% or less of the sum comprising the amount of the polypeptide with a mannose-5 glycostructure, the amount of the polypeptide G(0) isoform, the amount of the polypeptide G(1) isoform, and the amount of the polypeptide G(2) isoform after 7 days of cultivation.

17. The method according to claim 1, wherein the fraction of the immunoglobulin with a mannose-5 glycostructure is 6% or less of the sum comprising the amount of the polypeptide with a mannose-5 glycostructure, the amount of the polypeptide G(0) isoform, the amount of the polypeptide G(1) isoform, and the amount of the polypeptide G(2) isoform after 7 days of cultivation.

18. A method for the production of an immunoglobulin comprising
   a) cultivating a Chinese Hamster Ovary (CHO) cell comprising a nucleic acid encoding the immunoglobulin in a cultivation medium with restricted glucose feeding wherein the amount of glucose available in the cultivation medium per time unit is kept constant in all time units in which restricted glucose feeding is performed and the degree of glucose limitation (DGL) is limited to a single constant value in a range between 0.5 and 0.1, and wherein the restricted glucose feeding is started at day 2 or day 3 of the cultivating and wherein said cultivating is a fed-batch cultivating, and
   b) recovering the immunoglobulin.

19. The method according to claim 1, wherein the time unit is about 1 minute.

20. The method according to claim 1, wherein the time unit is about 1 hour.

21. The method according to claim 1, wherein the time unit is about 6 hours.

22. The method according to claim 1, wherein the time unit is about 12 hours.

23. The method according to claim 1, wherein the time unit is about 24 hours.

24. The method according to claim 1, wherein density of CHO cells at the beginning of the cultivating is about $10^5$ cells per milliliter.

25. The method according to claim 1, wherein density of CHO cells at the beginning of the cultivating is about $8 \times 10^5$ cells per milliliter.

26. The method according to claim 1, wherein density of CHO cells at the beginning of the cultivating is about $10 \times 10^5$ cells per milliliter.

27. The method according to claim 1, wherein density of CHO cells at the beginning of the cultivating is about $12 \times 10^5$ cells per milliliter.

28. The method according to claim 1, wherein density of CHO cells is from about $10^5$ cells per milliliter to about $60 \times 10^5$ cells per milliliter during the cultivation.

29. The method according to claim 18, wherein the time unit is about 1 minute.

30. The method according to claim 18, wherein the time unit is about 1 hour.

31. The method according to claim 18, wherein the time unit is about 6 hours.

32. The method according to claim 18, wherein the time unit is about 12 hours.

33. The method according to claim 18, wherein the time unit is about 24 hours.

34. The method according to claim 18, wherein density of CHO cells at the beginning of the cultivating is about $10^5$ cells per milliliter.

35. The method according to claim 18, wherein density of CHO cells at the beginning of the cultivating is about $8 \times 10^5$ cells per milliliter.

36. The method according to claim 18, wherein density of CHO cells at the beginning of the cultivating is about $10 \times 10^5$ cells per milliliter.

37. The method according to claim 18, wherein density of CHO cells at the beginning of the cultivating is about $12 \times 10^5$ cells per milliliter.

38. The method according to claim 18, wherein density of CHO cells is from about $10^5$ cells per milliliter to about $60 \times 10^5$ cells per milliliter during the cultivation.

39. The method according to claim 1, wherein cultivating the CHO cell is performed for six to fifteen days.

40. The method according to claim 1, wherein cultivating the CHO cell is performed for six to eight days.

41. The method according to claim 1, wherein the fraction of the immunoglobulin with a mannose-5 glycostructure is 8% or less of the sum comprising the amount of the polypeptide with a mannose-5 glycostructure, the amount of the polypeptide G(0) isoform, the amount of the polypeptide G(1) isoform, and the amount of the polypeptide G(2) isoform after 7 days of cultivation.

* * * * *